(12) United States Patent
Peyman

(10) Patent No.: US 9,814,567 B2
(45) Date of Patent: *Nov. 14, 2017

(54) METHOD OF ALTERING THE REFRACTIVE PROPERTIES OF AN EYE

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/186,331

(22) Filed: Jun. 17, 2016

(65) Prior Publication Data

US 2017/0007395 A1 Jan. 12, 2017

Related U.S. Application Data

(63) Continuation-in-part of application No. 14/960,409, filed on Dec. 6, 2015, now Pat. No. 9,370,446, which
(Continued)

(51) Int. Cl.
*A61F 2/14* (2006.01)
*A61F 9/008* (2006.01)
(Continued)

(52) U.S. Cl.
CPC ........ *A61F 2/1451* (2015.04); *A61F 9/00804* (2013.01); *A61F 9/00812* (2013.01);
(Continued)

(58) Field of Classification Search
CPC ........ A61F 2/142; A61F 2/145; A61F 2/1451; A61F 2/147; A61F 9/00804;
(Continued)

(56) References Cited

U.S. PATENT DOCUMENTS 3,760,807 A 9/1973 Neefe
4,665,913 A 5/1987 L'Esperance, Jr.
(Continued)

FOREIGN PATENT DOCUMENTS

WO 01/58495 A2 8/2001

OTHER PUBLICATIONS

J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).
(Continued)

*Primary Examiner* — Howie Matthews
(74) *Attorney, Agent, or Firm* — The Law Office of Patrick F. O'Reilly III, LLC

(57) ABSTRACT

The present invention relates to a method of altering the refractive properties of the eye, the method including forming a pocket in a cornea of an eye of a patient so as to gain access to tissue bounding the pocket; after the pocket in the cornea has been formed, applying a photosensitizer inside the pocket so that the photosensitizer permeates at least a portion of the tissue bounding the pocket, the photosensitizer facilitating cross-linking of the tissue bounding the pocket; inserting a lens implant into the pocket so as to change the refractive properties of the eye; and irradiating the cornea so as to activate cross-linkers in the portion of the tissue bounding the pocket and thereby stiffen the cornea and prevent corneal ectasia of the cornea.

21 Claims, 27 Drawing Sheets

Related U.S. Application Data is a continuation-in-part of application No. 14/874,453, filed on Oct. 4, 2015, now Pat. No. 9,681,984, which is a continuation-in-part of application No. 12/770,011, filed on Apr. 29, 2010, now Pat. No. 9,155,652, which is a continuation-in-part of application No. 12/608,249, filed on Oct. 29, 2009, now Pat. No. 9,681,942, which is a continuation-in-part of application No. 11/676,793, filed on Feb. 20, 2007, now abandoned, which is a continuation-in-part of application No. 11/446,065, filed on Jun. 1, 2006, now abandoned, which is a continuation-in-part of application No. 11/070,659, filed on Mar. 2, 2005, now abandoned, which is a continuation-in-part of application No. 09/986,141, filed on Nov. 7, 2001, now Pat. No. 6,918,904.

(51) Int. Cl.
| | | |
|---|---|---|
| *A61N 5/06* | (2006.01) | |
| *A61F 7/00* | (2006.01) | |
| *A61F 9/007* | (2006.01) | |
| *A61F 9/009* | (2006.01) | |
| *A61F 9/013* | (2006.01) | |

(52) U.S. Cl.
CPC .......... *A61F 9/00827* (2013.01); *A61F 7/007* (2013.01); *A61F 9/008* (2013.01); *A61F 9/009* (2013.01); *A61F 9/0079* (2013.01); *A61F 9/00821* (2013.01); *A61F 9/013* (2013.01); *A61F 9/0133* (2013.01); *A61F 2007/0004* (2013.01); *A61F 2007/0054* (2013.01); *A61F 2009/0088* (2013.01); *A61F 2009/00853* (2013.01); *A61F 2009/00872* (2013.01); *A61N 5/062* (2013.01)

(58) Field of Classification Search
CPC .............. A61F 9/00812; A61F 9/00853; A61F 9/00827; A61F 2009/00853
See application file for complete search history.

(56) References Cited

U.S. PATENT DOCUMENTS

| | | | |
|---|---|---|---|
| 4,718,418 | A | 1/1988 | L'Esperance, Jr. |
| 4,799,931 | A | 1/1989 | Lindstrom |
| 4,840,175 | A | 6/1989 | Peyman |
| 4,903,695 | A | 2/1990 | Warner et al. |
| 4,994,058 | A | 2/1991 | Raven et al. |
| 5,171,318 | A | 12/1992 | Gibson et al. |
| 5,336,261 | A | 8/1994 | Barrett et al. |
| 5,964,748 | A | 10/1999 | Peyman |
| 6,110,166 | A | 8/2000 | Juhasz |
| 6,197,019 | B1 | 3/2001 | Peyman |
| 6,537,545 | B1 | 3/2003 | Karageozian et al. |
| 6,551,307 | B2 | 4/2003 | Peyman |
| 7,001,374 | B2 | 2/2006 | Peyman |
| 7,004,902 | B2 | 2/2006 | Luce |
| 7,044,945 | B2 | 5/2006 | Sand |
| 2002/0006394 | A1 | 1/2002 | Redmond et al. |
| 2007/0135754 | A1 | 6/2007 | Akiyama et al. |
| 2009/0171305 | A1 | 7/2009 | El Hage |
| 2010/0210996 | A1 | 8/2010 | Peyman |
| 2011/0166650 | A1 | 7/2011 | Busin |
| 2011/0208300 | A1 | 8/2011 | de Juan, Jr. et al. |

OTHER PUBLICATIONS

Wollensak et al., "Riboflavin/Ultraviolet-A—induced Collagen Crosslinking for the Treatment of Keratoconus", American Journal of Ophthalmology, vol. 135, pp. 620-627 (2003).

Appeal Decision from the Patent Trial and Appeal Board in U.S. Appl. No. 12/770,011, dated on May 29, 2015.

M. A. Bamashmus, M. F. Saleh, M. A. Awadalla, "Reasons for Not Performing Keratorefractive Surgery in Patients Seeking Refractive Surgery in a Hospital-Based Cohort in Yemen", Middle East Afr J Ophthalmol, Oct.-Dec. 2010; 17(4): pp. 349-353.

Notice of Allowance in U.S. Appl. No. 12/608,249, dated Feb. 16, 2017.

Appeal Decision from the Patent Trial and Appeal Board in U.S. Appl. No. 12/608,249, dated Jan. 30, 2017.

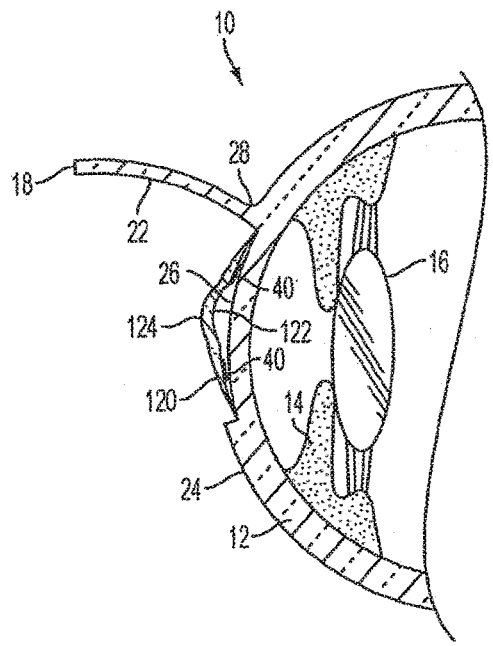 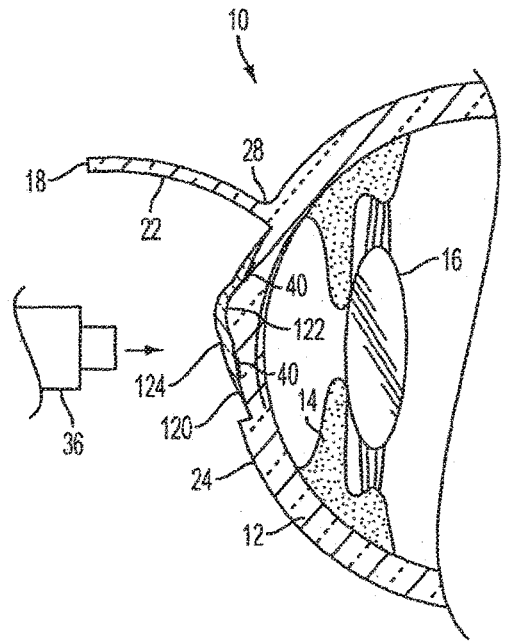
FIG. 9　　　　　FIG. 10
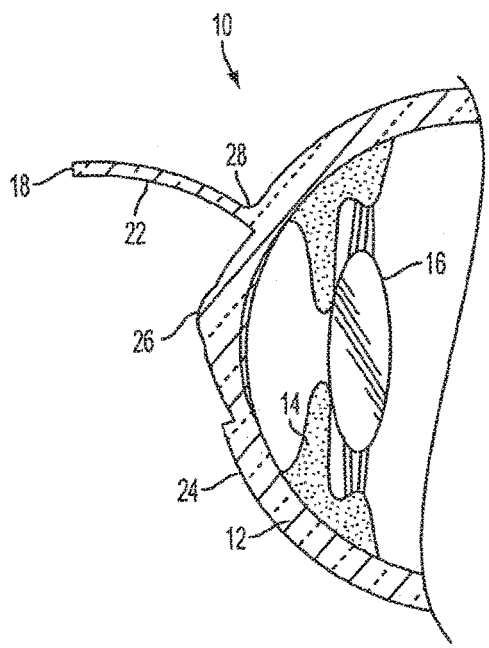 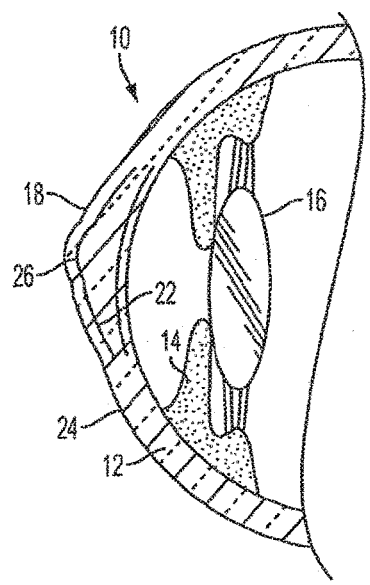
FIG. 11　　　　　FIG. 12

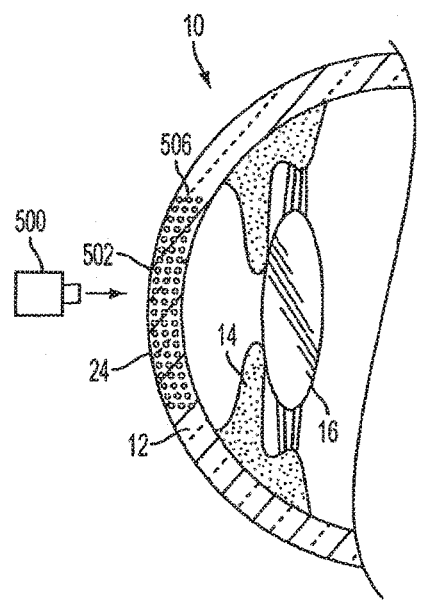
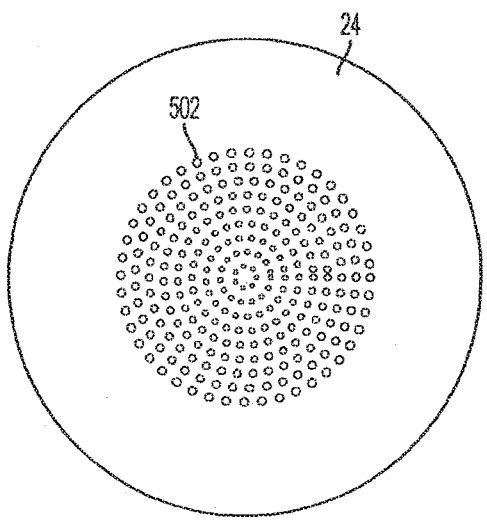
FIG. 21　　　　　　　FIG. 22
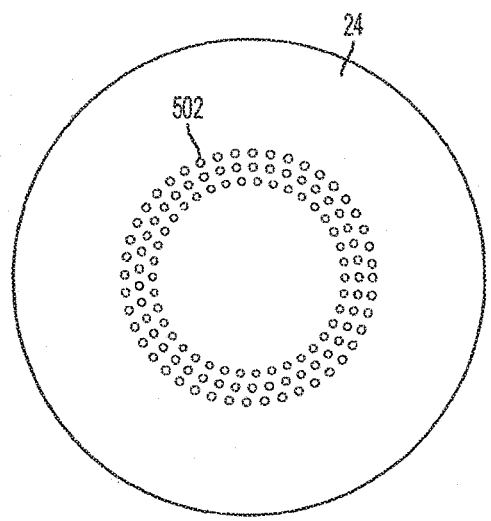
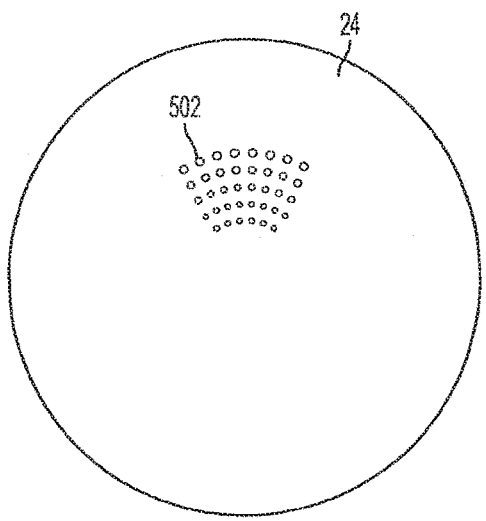
FIG. 23　　　　　　　FIG. 24

METHOD OF ALTERING THE REFRACTIVE PROPERTIES OF AN EYE

CROSS-REFERENCE TO RELATED APPLICATIONS

This application is a continuation-in-part of U.S. patent application Ser. No. 14/960,409, filed Dec. 6, 2015, entitled "Method of Altering the Refractive Properties of an Eye", which is a continuation-in-part of U.S. patent application Ser. No. 14/874,453, filed Oct. 4, 2015, entitled "Method of Altering the Refractive Properties of an Eye", which is a continuation-in-part of U.S. patent application Ser. No. 12/770,011, filed Apr. 29, 2010, entitled "Method for Laser Correction of Refractive Errors of an Eye with a Thin Cornea", now U.S. Pat. No. 9,155,652, which is a continuation-in-part of U.S. patent application Ser. No. 12/608,249, filed Oct. 29, 2009, entitled "Method for Prevention of Rejection and Sever Encapsulation of a Supportive or Functioning Implant", which is a continuation-in-part of U.S. patent application Ser. No. 11/676,793 filed Feb. 20, 2007, entitled "Method and System for Altering the Refractive Properties of the Eye", which is a continuation-in-part of U.S. patent application Ser. No. 11/446,065, filed Jun. 1, 2006, entitled "Device and Method for Reshaping the Cornea", which is a continuation-in-part of application of U.S. patent application Ser. No. 11/070,659, filed Mar. 2, 2005, entitled "Device and Method for Reshaping the Cornea", which is a continuation-in-part of U.S. patent application Ser. No. 09/986,141, filed Nov. 7, 2001, entitled "Method of Reshaping the Cornea by Controlled Thermal Delivery", now U.S. Pat. No. 6,918,904, the entire contents of each of which are incorporated herein by reference.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

A normal emmetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused behind the retina.

An eye suffering from astigmatism has a defect in the lens or shape of the cornea. Therefore, an astigmatic eye is incapable of sharply focusing images on the retina.

Optical methods are known which involve the placement of lenses in front of the eye, for example, in the form of eyeglasses or contact lenses, to correct vision disorders. A common method of correcting myopia is to place a "minus" or concave lens in front of the eye to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses.

Although these optical methods can be used to correct vision in eyes suffering from low myopia, or in eyes suffering from hypermetropic, hyperopic or astigmatic conditions which are not very severe, these methods are ineffective in correcting vision in eyes suffering from severe forms of ametropia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then thawed and reattached to the main portion of the live cornea. Hence, it is intended that the reshaped cornea will change the position at which the light entering the eye through the cut portion is focused, so that hopefully the light is focused directly on the retina, thus remedying the ametropic condition.

The myopic keratomileusis technique is known to be effective in curing myopic conditions within a high range. However, the technique is impractical because it employs very complicated and time consuming freezing, cutting and thawing processes.

Keratophakia is another known surgical technique for correcting severe ametropic conditions of the eye by altering the shape of the eye's cornea. In this technique an artificial, organic or synthetic lens is implanted inside the cornea to thereby alter the shape of the cornea and thus change its refractive power. Accordingly, as with the myopic keratomileusis technique, it is desirable that the shape of the cornea be altered to a degree that allows light entering the eye to be focused correctly on the retina.

However, the keratophakia technique is relatively impractical, complicated, and expensive because it requires manufacturing or cutting a special lens prior to its insertion into the cornea. Hence, a surgeon is required to either maintain an assortment of many differently shaped lenses, or alternatively, must have access to expensive equipment, such as a cryolathe, which can be used to cut the lens prior to insertion into the cornea.

Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., and a publication by Jose I. Barraquer, M. D. entitled "Keratomileusis and Keratophakia in the Surgical Correction of Aphakia". The entire contents of each of these patents are incorporated herein by reference.

Surgical techniques involving the use of ultraviolet and shorter wavelength lasers to modify the shape of the cornea also are known. For example, excimer lasers, such as those described in U.S. Pat. No. 4,840,175 to Peyman, which emit pulsed ultraviolet radiation, can be used to decompose or photoablate tissue in the live cornea so as to reshape the cornea.

Specifically, a laser surgical technique known as laser in situ keratomileusis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150-180 microns deep. The cut portion is then reattached over the ablated portion of the cornea and assumes a shape conforming to that of the ablated portion.

However, because only a certain amount of cornea can be ablated without the remaining cornea becoming unstable or experiencing outwardbulging (ectasia), this technique is not especially effective in correcting very high myopia. That is, a typical live cornea is on average about 500 microns thick. The laser ablation technique requires that at least about 200 microns of the corneal stroma remain after the ablation is completed so that instability and outwardbulging does not occur. Hence, this method typically cannot be effectively used to correct high myopia of greater than 15 diopters because, in order to reshape the cornea to the degree necessary to alter its refractive power to sufficiently correct the focusing of the eye, too much of the cornea would need to be ablated.

Additionally, the cornea can be modified using thermal coagulation. In thermal coagulation, electrodes of varying shapes are applied to the cornea in a predetermined pattern. The electrodes emit a radio frequency wave or laser light, thereby heating the surface of the cornea. Once the surface of the cornea is heated it tends to shrink, the shrinking of the cornea changes the refractive properties of the eye. In these methods, the thermal temperature generally rises in the surface of the cornea and in the deeper tissue above the coagulation threshold, producing clinical appearance of a gray to white response in the cornea, or protein denaturation. Furthermore, since the cornea can generally only be shrunk in response to thermal coagulation, this method is exclusively used for presbyopic and hyperopic correction of refractive errors.

Therefore, it is apparent that a need therefore exists for improved methods for further modifying the cornea to better correct ametropic conditions.

BRIEF SUMMARY OF EMBODIMENTS OF THE INVENTION

Accordingly, the present invention is directed to a method of altering the refractive properties of the eye that substantially obviates one or more problems resulting from the limitations and deficiencies of the related art.

In accordance with one or more embodiments of the present invention, there is provided a method of altering the refractive properties of the eye. The method comprising the steps of: (i) forming a pocket in a cornea of an eye of a patient so as to gain access to tissue bounding the pocket, wherein the forming of the pocket in the cornea of the eye severs some corneal nerves supplying a front surface of the cornea so as to reduce the postoperative pain sensation that is felt by the patient, but does not sever all of the corneal nerves supplying the front surface of the cornea so as to prevent a formation of dry eye in the patient; (ii) after the pocket in the cornea has been formed, applying a photosensitizer inside the pocket so that the photosensitizer permeates at least a portion of the tissue bounding the pocket, the photosensitizer facilitating cross-linking of the tissue bounding the pocket; (iii) inserting a lens implant into the pocket so as to change the refractive properties of the eye; and (iv) irradiating the cornea so as to activate cross-linkers in the portion of the tissue bounding the pocket and thereby stiffen the cornea and prevent corneal ectasia of the cornea. In these one or more embodiments, the cross-linking of the tissue bounding the pocket does not adhere the lens implant to the tissue bounding the pocket so that the lens implant is capable of subsequently replaced if needed, and the cross-linking of the tissue bounding the pocket does not adhere spaced apart portions of the tissue bounding the pocket to one another.

In a further embodiment of the present invention, the step of forming the pocket in the cornea of the eye severs less than one-half of the corneal nerves supplying the anterior corneal sub-epithelial plexus so as to prevent the formation of dry eye in the patient.

In yet a further embodiment, the step of forming the pocket in the cornea of the eye comprises forming the pocket in stromal tissue of the cornea.

In still a further embodiment, the pocket formed in the cornea of the eye has a diameter between about 1 millimeter and about 12 millimeters.

In yet a further embodiment, the pocket formed in the cornea of the eye has a shape selected from the group consisting of: (i) a disk shape, (ii) a ring or doughnut shape, and (iii) a sectorial shape.

In still a further embodiment, the photosensitizer comprises riboflavin in a biocompatible fluid, the riboflavin being provided in a concentration of between approximately 0.2% and approximately 4.0% in the biocompatible fluid; and the step of applying the photosensitizer inside the pocket comprises injecting the biocompatible fluid containing the riboflavin inside the pocket using a needle.

In yet a further embodiment, the biocompatible fluid containing the riboflavin is injected into the pocket for a time duration that is sufficient to enable the riboflavin to penetrate at least 20 microns into the tissue bounding the pocket.

In still a further embodiment, the method further comprises the step of: (v) applying the photosensitizer inside the pocket one or more additional times and irradiating the cornea one or more additional times to cross-link the tissue bounding the pocket so as to prevent any cellular invasion in an area surrounding the lens implant after the initial implantation of the lens implant.

In yet a further embodiment, the lens implant has a thickness between approximately 10 microns and approximately 400 microns.

In still a further embodiment, the lens implant has a shape selected from the group consisting of: (i) a disk shape, (ii) a ring or doughnut shape, and (iii) a sectorial shape.

In yet a further embodiment, the method further comprises the step of: (v) replacing the lens implant with a new lens implant in order to correct the remaining refractive error of the eye or to correct a new refractive error that has developed in the eye.

In still a further embodiment, the lens implant has a predetermined refractive index and a predetermined curvature, and wherein one or both of the predetermined refractive index and the predetermined curvature of the lens implant are used to change the refractive properties of the eye.

In yet a further embodiment, the lens implant is formed from a transparent organic biocompatible material, a transparent synthetic biocompatible material, or a combination of a transparent organic biocompatible material and a transparent synthetic biocompatible material.

In still a further embodiment, the lens implant has a plurality of holes disposed therein, each of the plurality of holes having a hole diameter between approximately 0.1 microns and approximately 100 microns.

In yet a further embodiment, the lens implant comprises a first subset of the plurality of holes within a central region and a second subset of the plurality of holes within a peripheral region outside the central region, the central region having a diameter of 5 millimeters; and each of the first subset of the plurality of holes has a hole diameter between approximately 0.1 microns and approximately 4 microns, and each of the second subset of the plurality of holes has a hole diameter between approximately 1 micron and approximately 100 microns.

In still a further embodiment, the lens implant has a dioptric power between −20 diopters and +20 diopters for spherical correction and a dioptric power between −6 diopters and +6 diopters for correction of astigmatism.

In yet a further embodiment, the lens implant is disposed in a corneal location selected from the group consisting of: (i) a center location over the visual axis of the eye for correcting myopia, hyperopia, or astigmatism, (ii) an off-center location from the visual axis of the eye for correcting for correcting presbyopia eyes, (iii) a location surrounding a central portion of the cornea, but not overlapping the visual axis of the eye for creating a bifocal cornea, (iv) a location circumscribing a peripheral portion of the cornea for treating a peripheral degenerative corneal disease, and (v) a peripheral location overlapping a sectorial portion of the cornea.

In still a further embodiment, the lens implant comprises a circular plate made of a cross-linked collagen so as to add structural rigidity to the cornea of the eye; and the method further comprises the step of: (v) implanting a mesh formed from nanoparticles into the pocket formed in the cornea so as to add further structural rigidity to the cornea of the eye.

In yet a further embodiment, the nanoparticles forming the mesh comprise graphene.

In still a further embodiment, the method further comprises the step of: (v) after the lens implant has been inserted into the pocket, ablating the front surface of the cornea so as to further alter the refractive properties of the eye and to eliminate any residual refractive error remaining after initial refractive error correction by the lens implant.

In yet a further embodiment, the step of ablating a front surface of the cornea so as to change the refractive properties of the eye comprises performing a mini-photorefractive keratectomy (mini-PRK) procedure on the front surface of the cornea, the mini-PRK procedure being limited to a central region of the cornea having a diameter between approximately 3 millimeters and 5 millimeters, and the mini-PRK procedure resulting in a dioptric power correction of between 0.2 diopters and 2 diopters.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 9 is a side elevational view in cross section of the eye of FIG. 8 with the reshaping device immediately adjacent and overlying the exposed surface of the cornea;

FIG. 10 is a side elevational view in cross section of the eye of FIG. 9 with a laser irradiating the surface of the cornea to cross link the cornea with the cross linked portion of the cornea conforming to the internal shape of the reshaping device;

FIG. 11 is a side elevational view in cross section of the eye of FIG. 10 with the reshaping device removed and the cornea maintaining its reformed shape;

FIG. 12 is a side elevational view in cross section of the eye of FIG. 11 with the flap repositioned over the reformed exposed surface of the cornea;

FIG. 21 is a side elevational view in cross section of the eye of FIG. 1 with multiple cavities formed in the cornea via an ultra-short pulse laser;

FIG. 22 is a front view of the eye of FIG. 21 showing the multiple cavities forming a substantially circular pattern;

FIG. 23 is a front view of an eye having multiple cavities formed using an ultra-short pulse laser as shown in FIG. 21, the cavities forming a substantially ring-shaped configuration;

FIG. 24 is a front view of an eye having multiple cavities formed using an ultra-short pulse laser as shown in FIG. 21, the cavities formed in an area offset from the main optical axis;

Throughout the figures, the same elements are always denoted using the same reference characters so that, as a general rule, they will only be described once.

DETAILED DESCRIPTION OF EMBODIMENTS OF THE INVENTION

1. FIGS. 1-7

Figure 1:
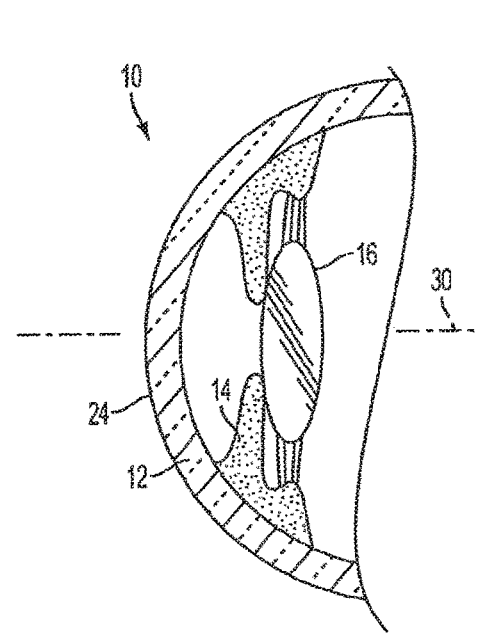
FIG. 1 is a side elevational view in cross section taken through the center of an eye showing the cornea, pupil and lens.

FIG. 1 is a side elevational view in cross section taken through the center of an eye 10, which includes a cornea 12, a pupil 14 and a lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

As seen in FIGS. 1-7, the refractive properties of the eye can be modified or altered by forming a flap 18 in the surface 12 of the cornea, preferably by placing a reshaping device 20 having a predetermined shape on the surface 12 of the cornea, heating the reshaping device and in turn heating the surface of the cornea. However, it is noted that the cornea can be heated by any means suitable, such as directly by a laser or chemically or any other method that would allow heating the cornea to the proper temperature. Heating the cornea to the predetermined temperature causes the corneal stroma to cross link and have a gel-like or gelatinous consistency. The gelatinous corneal portion then can flow and reform to take the form of the interior surface 32 of the reshaping device, thus changing the refractive properties of the cornea and the eye.

To begin, the refractive error in the eye is measured using wavefront technology, as is known to one of ordinary skill in the art. The refractive error measurements are used to determine the appropriate shape of lens or contact 20 to best correct the error in the patient's cornea. Preferably, the lens 20 is manufactured or shaped prior to the use of the wavefront technology and is stored in a sterilized manner until that specific lens shape or size is needed. However, the information received during the measurements from the wavefront technology can be used to form the lens using a cryolathe, or any other desired system or machine.

Figure 2:
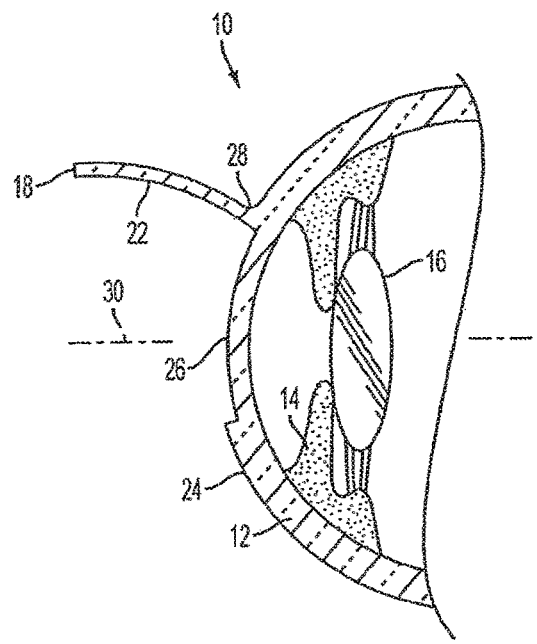
FIG. 2 is a side elevational view in cross section of the eye of FIG. 1 with a flap formed in the surface of the cornea.
Figure 3:
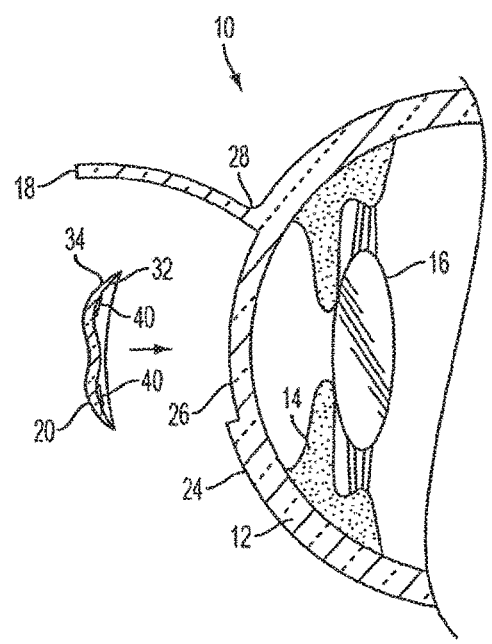
FIG. 3 is a side elevational view in cross section of the eye of FIG. 2 with a reshaping device having a predetermined shape for correcting myopia proximate to the exposed surface of the cornea.

In one embodiment, a flap or portion 18 can be formed in the surface 24 of the cornea 12, as seen in FIG. 2. The flap may be formed in the stromal layer of the cornea, but does not necessarily need to be formed in the stromal layer and can be formed in any desired portion of the cornea, such as the epithelium or any other portion desired. The flap may be formed be any means desired, such as with a knife, microkeratome, or with a laser. An internal area of the cornea is separated into first and second substantially circular shaped internal surfaces 22 and 26, respectively, to form the circular shaped corneal flap 18. First internal surface 22 faces in a posterior direction of cornea 12 and the second internal surface 26 faces in anterior direction of the cornea 12. The flap 18 can have a uniform thickness of about 10-250 microns, and preferably about 80-100 microns, but can be any suitable thickness. If the flap embodiment is used, a portion 28 of flap 18 preferably remains attached to the cornea by an area at the periphery of the flap. However, the flap can be any suitable configuration, such as a flap attached to the cornea at a location other than at the periphery or a flap that is not attached to the cornea at all. Additionally, the flap may be shaped or sized as desired and does not need to be circular.

The flap is moved or pivoted about portion 28 using any device known in the art, such as a spatula or microforceps or any other device, to expose the first and second corneal surfaces 22 and 26, respectively. The flap preferably exposes a portion of the corneal surface that intersects the main optical axis 30 and allows uninhibited access thereto.

Figure 4:
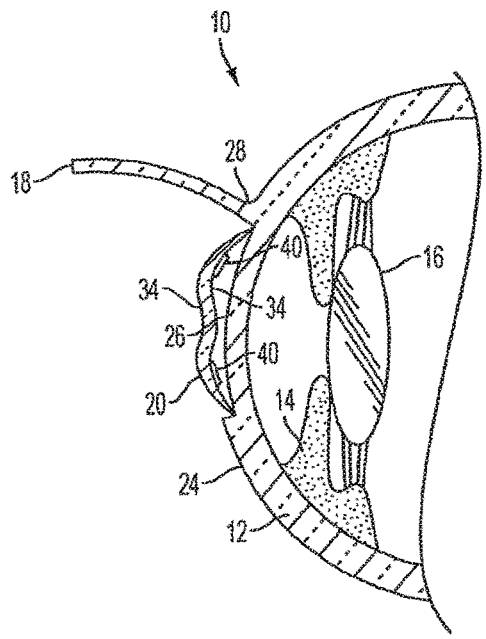
FIG. 4 is a side elevational view in cross section of the eye of FIG. 3 with the reshaping device immediately adjacent and overlying the exposed surface of the cornea.

Lens or mold 20 can then be positioned adjacent and overlying the surface 26 of the cornea, as seen in FIG. 4. However, it is noted that the lens does not necessarily need to be positioned adjacent a surface exposed by a flap and may be positioned on the external surface 24 of the cornea 12, as described below, or the second internal surface 26.

Lens 20 is preferably any metal that can absorb heat and transmit and distribute heat throughout the lens in a uniform or substantially uniform manner. However, the lens does not necessarily need to be metal and can be any synthetic or semi-synthetic material, such as plastic or any polymer or any material that has pigmentation that would allow the lens to absorb the heat from the laser and transmit and distribute the heat uniformly throughout the lens.

Additionally, lens 20 is substantially circular and has a first or inner side or surface 32 and a second or outer side or surface 34 and preferably has a substantially concave shape. The lens preferably has a predetermined shaped, or more specifically, the first surface 32 preferably has a predetermined shape that would be the proper shape of the surface 26 of the cornea plus the flap 18 to focus light onto the retina. In other words, if the interior of the cornea were the shape of the interior surface of the lens the patient would be able to have 20/20 vision or better.

FIGS. 1-7 show the correction of myopic error using a concave lens 20. However, the lens can be formed such as lens 120, shown in FIGS. 8-12 and discussed below, for correction of hyperopic error or any other shape desired for the correction of astigmatic error, presbyopia or any other error.

Figure 5:
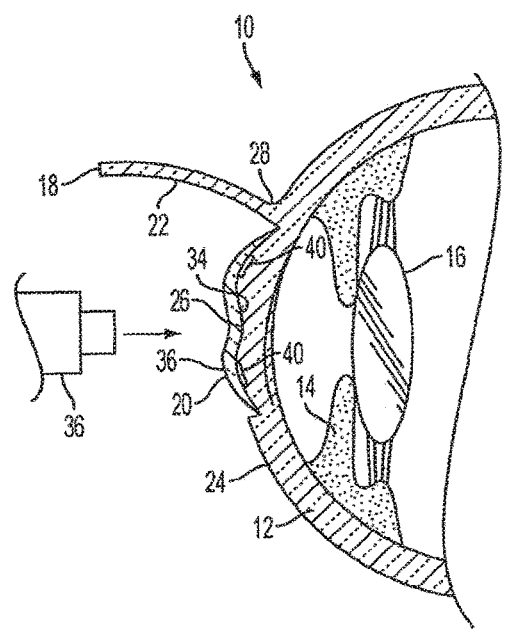
FIG. 5 is a side elevational view in cross section of the eye of FIG. 4 with a laser irradiating the reshaping device to cross link the cornea with the cross linked portion of the cornea conforming to the internal shape of the reshaping device.

Once the reshaping device is positioned immediately adjacent a surface of the cornea 12, a heating device is applied or administered to the reshaping device 20, which in turn transfers the heat to the surface of the cornea. Preferably as seen in FIG. 5, a laser 36 is aimed and fired or directed, so that the light emitted from the laser or the laser beam L is absorbed by the reshaping device 20 and then absorbed by or transferred to the cornea. Preferably, the laser beam is in the infrared portion of the electromagnetic spectrum, such as light supplied by a Nd-Yag laser at 1.32 μm, a Holmium laser at 2.2 μm or a Erb-Yag laser at 2.9 μm, or any other laser light wave length that is absorbed by water. For example, the laser light can be from a $CO_2$ laser or a visible light laser, such as an argon laser. Additionally, the reshaping device can be heated by any means suitable, such as microwaves.

The laser beam preferably heats the lens so that the inner surface of the reshaping device is about or below 60.degree. Celsius (140.degree. F.), which in turn heats the corneal surface (such as the stroma or the external surface of the cornea) to about the same temperature, thereby cross linking the cornea. The reshaping device inner surface temperature can be constantly controlled or measured, for example, using one or multiple thermal couples 40 on the inner surface of the reshaping device. The thermal couples are linked to a computer control system (not shown) using any method known in the art, such as direct electrical connection or wires or a wireless system. The computer control system monitors (or enables a user to monitor) the temperature and controls (or enables a user to control) the laser to change the temperature of the reshaping device. The computer can maintain a precise constant temperature, increase temperature or decrease temperature as desired, and at any rate desired. This computer control system, along with the thermal couples, ensures an adequate and precise temperature, since heating the cornea above 60.degree. Celsius can cause coagulation of the cornea.

Figure 6:
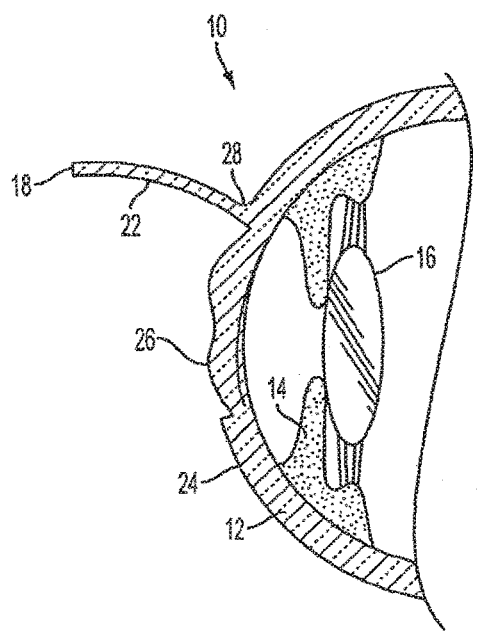
FIG. 6 is a side elevational view in cross section of the eye of FIG. 5 with the reshaping device removed and the cornea maintaining its reformed shape.

By heating the corneal stroma to about or below 60 degree C., the molecules of the cornea are loosened, and the cornea changes from a substantially solid substance to a gelatinous substance or gel-like substance. However, the corneal temperature is maintained at or below 60.degree. C., and therefore, protein denaturation does not occur as with conventional thermal coagulation. Under this system, the cornea reforms and is molded to take the shape of the inner surface 32 of the reshaping device, thereby forming the cornea into the reformed, corrected shape in an effort to provide the patient with 20/20 vision. The cornea can then cooled by applying cool or cold water, by applying air or by simply removing the heated reshaping device or the heat from the reshaping device and using the ambient air temperature. As the cornea cools, it is held by the reshaping device 20 to the preferred shape, which becomes its new permanent shape once the cornea is completely cooled and changes from its gel-like consistency to its original substantially solid consistency, as shown in FIG. 6.

Figure 7:
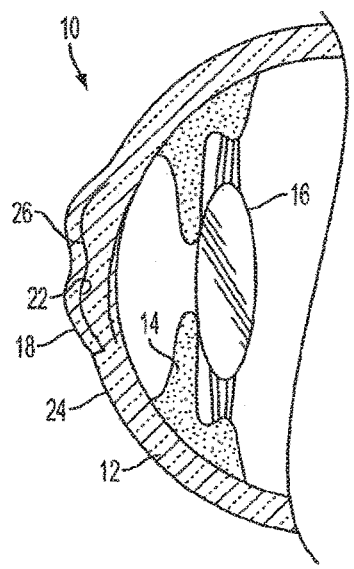
FIG. 7 is a side elevational view in cross section of the eye of FIG. 6 with the flap repositioned over the reformed exposed surface of the cornea.
Figure 8:
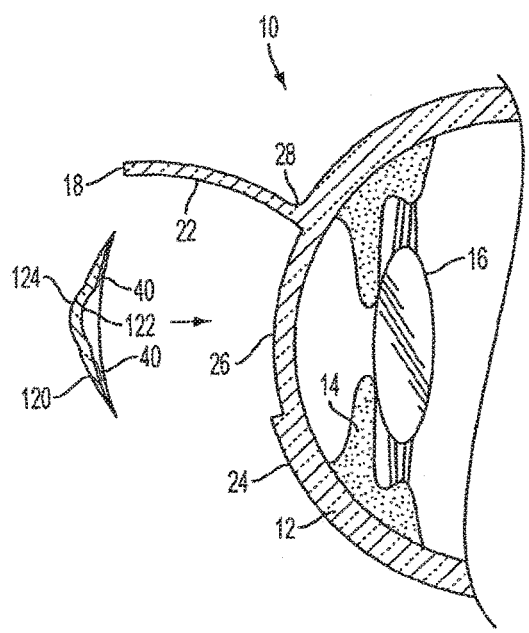
FIG. 8 is a side elevational view in cross section of the eye of FIG. 2 with a reshaping device having a predetermined shape for correcting hyperopia proximate to the exposed surface of the cornea.

The flap 18 can then be replaced so that it covers or lies over the first surface 26 of the cornea 12 in a relaxed state, as seen in FIG. 7. This new permanent shape allows the cornea to properly focus light entering the eye on the retina. The refractive power of the eye is then measured to determine the extent of the correction. If necessary the method can be repeated.

A reshaping lens can be applied to the external surface of the cornea, if desired, after the flap has been replaced to maintain the proper corneal curvature or the eye can be left to heal with no additional reshaping lens being used.

Furthermore, at the end of the method, if desired, topical agents, such as an anti-inflammatory, antibiotics and/or an antiprolifrative agent, such as mitomycin or thiotepa, at very low concentrations can be used over the ablated area to prevent subsequent haze formation. The mitomycin concentration is preferably about 0.005-0.05% and more preferably about 0.02%. A short-term bandage contact lens may also be used to protect the cornea.

By reforming the cornea into the desired shape in this manner, a highly effective surgical method is formed that allows perfect or near perfect vision correction without the need to ablate any of the cornea or causing a gray to white response in the cornea of the eye.

2. FIGS. 8-12

As shown in FIGS. 8-12, the same general method as shown in FIGS. 1-7 can be used to correct hyperopic error in the cornea. In this method, a substantially circular convex reshaping device 120, rather than concave reshaping device 20, having a first or inner surface 122 and a second or outer surface 124, is used and placed immediately adjacent and overlying the surface 26 of the cornea. A heating element, such as a laser 36 (or any other suitable device or method), is used to heat the reshaping device, which in turn increases the temperature of the cornea to about or below 60.degree. Celsius, as described above. This heating causes the cornea to cross link and turn into a gel-like material, thereby conforming to the inner surface 122. Once the corneal surface 26 cools and is permanently or semi-permanently reformed to the inner surface of the reshaping device, the device is removed and the flap replaced, if the flap method is used. The hyperopic error is corrected and the cornea can now effectively focus light on the retina, as described above.

This method for correcting hyperopic conditions is substantially similar to the method for correcting myopic conditions. Thus, the entire method described above for correcting myopic error of the cornea applies to the correction of hyperopic error, except for the exact configuration of the reshaping device.

Figure 13:
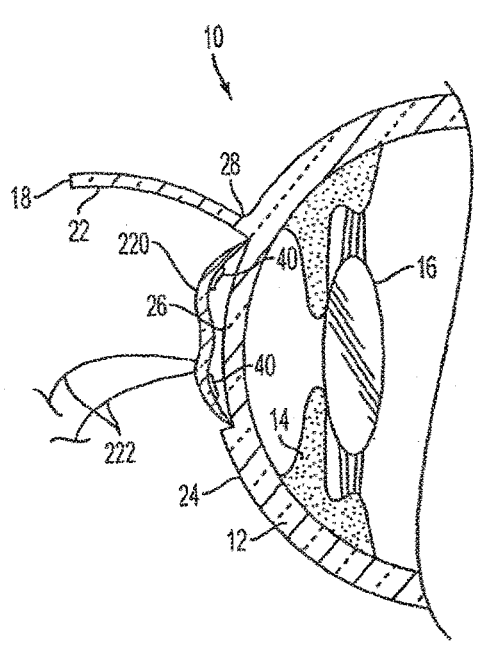
FIG. 13 is a side elevational view in cross section of the eye of FIG. 2 with a thermally conductive reshaping device having a predetermined shape immediately adjacent the exposed surface of the cornea.
Figure 14:
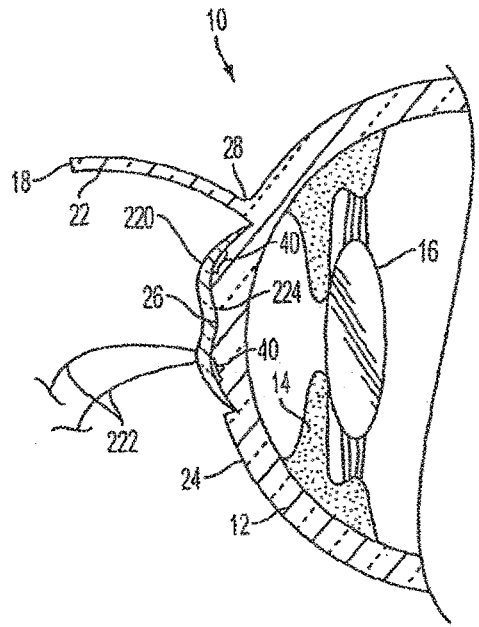
FIG. 14 is a side elevational view in cross section of the eye of FIG. 13 with the thermally conductive reshaping device administering controlled heat to the exposed surface of the cornea to cross link the cornea with the cross linked portion of the cornea conforming to the internal shape of the reshaping device.

3. FIGS. 13 and 14

As shown in FIGS. 13 and 14, the reshaping device can be a thermally conductive plate or reshaping device 220 that is electrically connected to a power source (not shown) using electrical wires 222. The thermally conductive plate 220 is preferably any metal or conductive material that can conduct electricity supplied by a power source (not shown) and turn the electricity into heat. Furthermore, the plate preferably is formed from a material that would allow an equal or substantially uniform distribution of heat through the plate.

This method is similar to those described above; however, the temperature of the cornea is increased using the thermocouple plate instead of a laser. As seen in FIG. 13, the plate 220 is heated to the desired temperature, preferably about or below 60 degrees Celsius, as described above. This causes loosening of the corneal molecules or cross linking of the cornea, which allows the cornea to conform to surface 224 of plate 220, thereby permanently changing the shape of the cornea. Once the corneal surface 26 has cooled and permanently reformed to the inner surface of the thermocouple plate, the plate is removed and the flap replaced, if this method is used. The cornea can now effectively focus light on the retina, as described above.

Although, the method is shown in FIGS. 13 and 14 using a thermally conductive plate to correct myopic error, a thermally conductive plate can be used to change the shape of the cornea in any manner desired, such to correct astigmatic or hyperopic error in the cornea.

Furthermore, since this method is substantially similar to the methods described above, the description of those methods and references numerals used therein, excluding the specific lens and heating element, apply to this method.

Figure 15:
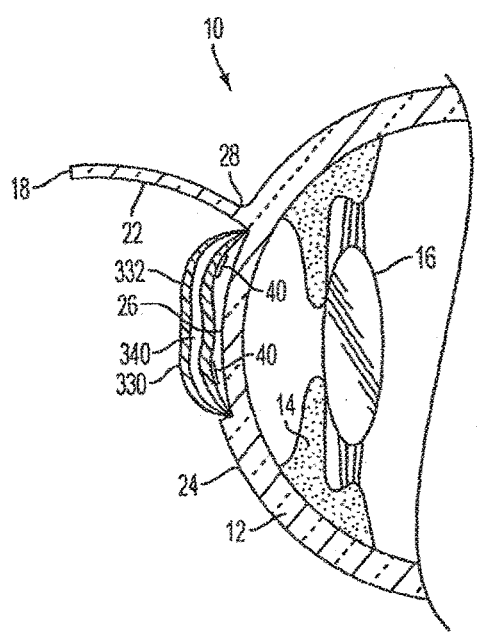
FIG. 15 is a side elevational view in cross section of the eye of FIG. 2 with a reshaping device having two passageways for irrigation and aspiration of a liquid with a predetermined temperature and having a predetermined shape immediately adjacent the exposed surface of the cornea.
Figure 16:
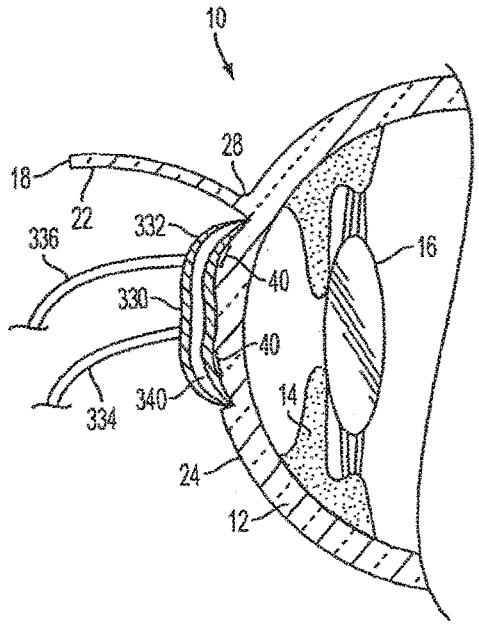
FIG. 16 is a side elevational view in cross section of the eye of FIG. 15 with the aspiration and irrigation tubes extending through the reshaping device for administering and removing liquid with a predetermined temperature to the exposed surface of the cornea to cross link the cornea with the cross linked portion of the cornea conforming to the internal shape of the reshaping device.
Figure 17:
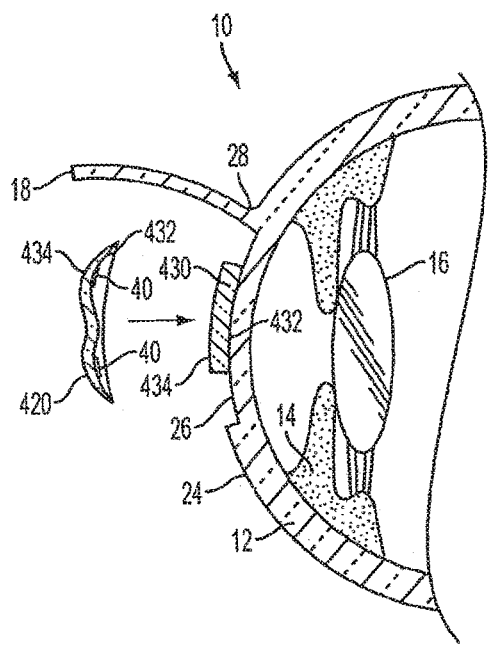
FIG. 17 is a side elevational view in cross section of the eye of FIG. 2 with a inlay positioned on the exposed surface of the cornea and with a reshaping device having a predetermined shape for correcting myopia proximate to the inlay.
Figure 18:
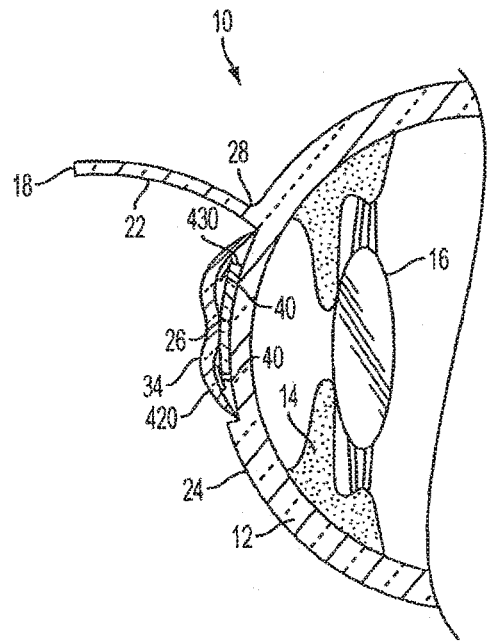
FIG. 18 is a side elevational view in cross section of the eye of FIG. 17 with the reshaping device immediately adjacent the inlay.
Figure 19:
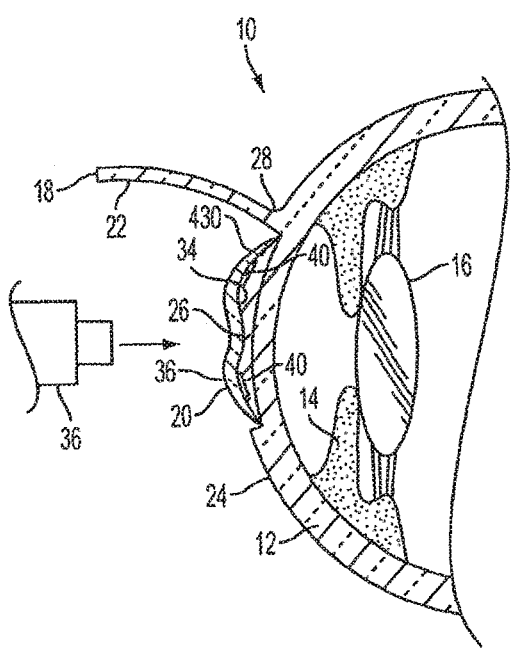
FIG. 19 is a side elevational view in cross section of the eye of FIG. 18 with a laser irradiating the lens to soften the inlay with the softened portion of the inlay conforming to the internal shape of the lens.

4. FIGS. 15 and 16

As shown in FIGS. 15 and 16, reshaping device 320 can be a container, i.e., hollow, with an irrigation port 330 and an aspiration port 332 providing access to interior chamber 340. Reshaping device 320 is preferably any metal or plastic that can be filled with a liquid and absorb heat and distribute the heat throughout the reshaping device in a uniform or substantially uniform manner. However, the reshaping device does not necessarily need to be metal and can be any synthetic or semi-synthetic material, such as plastic or any polymer or any material that would allow the lens to absorb the heat from the liquid and distribute the heat uniformly throughout the reshaping device.

The method of FIGS. 15-16 is similar to those described above; however, the temperature of the cornea is increased using a tube 334 that couples to the irrigation port and fills chamber 340 of the container with a liquid of a predetermined temperature, preferably about or below 60.degree. Celsius (140.degree. F.). Once filled with the liquid, the inner surface of the reshaping device would increase to the desired temperature, thereby loosening the molecules of the cornea or cross linking surface 26 of the cornea, which allows the cornea to conform to surface 324 of reshaping device 320 and results in the proper reformation of the cornea. The liquid can then be removed from the container via the aspiration tube 236, allowing the cornea to cool and permanently reform to the desired shape, as described above. Once the corneal surface 26 has cooled and permanently or semi-permanently reformed to the inner surface of the reshaping device, the reshaping device is removed and the flap replaced, if this method is used. The cornea can now effectively focus light on the retina, as described above.

Although, the method shown in FIGS. 15 and 16 uses a container to correct myopic error, this method can be used to change the shape of the cornea in any manner desired, such to correct astigmatic or hyperopic error in the cornea.

Furthermore, since this method is substantially similar to the methods described above, the description of those methods along with the reference numerals used therein, excluding the specific reshaping device and heating element, apply to this method.

5. FIGS. 17-20

As seen in FIGS. 17-20, a modified method does not necessarily need to be performed on the cornea, but can be performed on a separate lens or inlay 430. Inlay 430 is preferably a substantially circular polymeric or synthetic inlay or blank that has a predetermined thickness and a first side 432 and a second side 434 and is positioned under the flap adjacent second surface 26 to correct refractive error in the eye. For a more complete description of use of an inlay, see U.S. Pat. No. 6,197,019 to Peyman, the entire contents of which are herein incorporated by reference.

As described above and seen in FIGS. 18 and 19, a reshaping device 420 having a first surface 432 and a second surface 434 is placed over the inlay 430 adjacent surface 434 and heated to the appropriate temperature using a laser 36. Since the inlay is a polymer and is not formed from living cells, there is no need to keep the temperature at or about 60.degree. Celsius (140.degree. F.). The rise in temperature of the lens causes the inlay 430 to cross link or become a gelatinous material, which allows the inlay to conform to the shape of the inner surface 422 of reshaping device 420, in a similar manner to that described for the cornea above.

Figure 20:
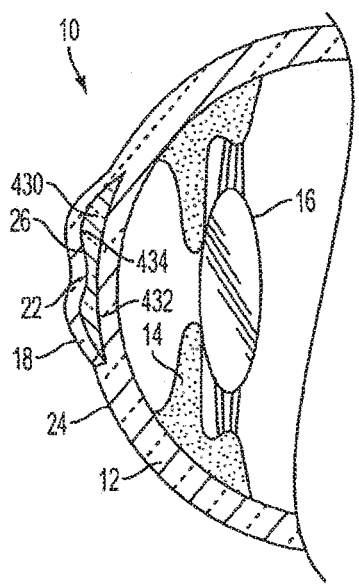
FIG. 20 is a side elevational view in cross section of the eye of FIG. 19 with the lens removed and the flap repositioned over the reformed inlay.

As seen in FIG. 20, once the reshaping device 420 is removed, the flap 18 can placed over the inlay 430. First internal surface 22 is positioned so that it overlies the second surface 434 of inlay 430 without substantial tension thereon. In other words, the flap is merely laid over top of the inlay 430 so as to not cause undue stress or tension in the flap and possibly causing damage thereto.

It is noted that the method of FIGS. 17-20 is not limited to the first herein described method using a reshaping device and a laser, but can be used with any heating means, such as the container method and the thermally conductive plate method also described herein and any other method that would heat a reshaping device overlying the inlay to the appropriate temperature.

Additionally, this method of FIGS. 17-20 can be performed with a lens that has a predetermined refractive index, is a blank having no refractive index or a lens that has been modified by a laser, a cryolathe or any other method known in the art to have a predetermined refractive index. For example, with a blank, the inlay can have no refractive power, the entire corrective change in the lens coming from the conformation to the inner surface of reshaping device 420 or the inlay can have refractive power with the reshaping device 420 simply modifying the refractive properties. Additionally, it is not necessary for this lens to be positioned between layers of the cornea. The lens can be positioned in any suitable position within the eye or in a position that is adjacent and external to the eye.

Although, the method shown in FIGS. 17-20 uses a lens to correct myopic error, this method can be used to change the shape of the cornea in any manner desired, such as to correct astigmatic or hyperopic error in the cornea.

Furthermore, since this method is substantially similar to the methods described above, the description of those methods along with the reference numerals used therein apply to this method.

6. FIGS. 21-29

FIGS. 21-29 illustrate another embodiment of the present invention for correcting refractive error in the eye, wherein a laser 500, such as a short pulse laser, is used to form cavities or three dimensional portions 502 in the cornea 12 of an eye 10. A mold or lens 504 is then used to reshape the cornea to correct the refractive error in the eye.

First, as described above the refractive error in the eye is measured using wavefront technology, as is known to one of ordinary skill in the art or any other suitable method. The refractive error measurements are used to determine the appropriate shape of lens or contact 504 to best correct the error in the patient's cornea 12. Preferably, the lens or reshaping device 504 is manufactured or shaped prior to the use of the wavefront technology and is stored in a sterilized manner until that specific lens shape or size is needed. However, the information received during the measurements from the wavefront technology can be used to form the lens using a cryolathe, laser, or any other desired system, method or machine.

Preferably lens 504 is preferably clear and formed from any organic, synthetic or semi-synthetic material or combination thereof, such as plastic or any polymer or any material that has pigmentation that would allow laser light to pass therethough such that laser light could heat the cornea as described herein. Lens 504 has a first surface 520 and a second surface 522. The second surface preferably is adapted to be positioned adjacent a surface of the cornea and has a predetermined curvature that will change the curvature of the cornea to correct refractive error. However, the lens does not necessarily need to be formed in this manner and can be opaque, translucent and/or formed in any manner described above or in any manner suitable for changing the curvature of the cornea.

As shown in FIG. 21, the laser 500 is preferably fired at a portion 506 of the cornea beneath or under the exterior surface 24 of the cornea, forming a predetermined pattern of cavities, which have a predetermined size and shape. In other words, the laser 500 is preferably fired at the stromal layer of the cornea. The laser is programmed to form up to about 10,000 small cavities or three dimensional aberrations 502 in the stroma of the eye. Each cavity has a diameter of about 10 microns or less to about 1 millimeter. It is noted that cavities 502 do not necessarily need to be formed in the stroma and can be formed in any portion of the cornea, such as in the Bowman's layer, the epithelial layer, or suitable portion of the eye or any combination thereof.

Laser 500 is preferably an ultra-short pulse laser, such as a femto, pico, or attosecond laser; but may be any light emitting device suitable for creating cavities 502. The ultra-short pulse laser 500 is positioned in front of the eye and focuses the laser beam in the cornea 12 at the desired depth for creating multiple cavities. Ultra short pulse lasers are desired since they are capable of ablating or vaporizing corneal tissue beneath the surface of the cornea without disrupting, damaging or affecting the surface of the cornea. Additionally, ultra short pulse lasers are high precision lasers that require less energy than conventional lasers to cut tissue and do not create "shock waves" that can damage surrounding structures. Cuts or ablation performed using ultra short pulse lasers can have very high surface quality with accuracy better than 10 microns, resulting in more precise cuts than those made with mechanical devices or other lasers. This type of accuracy results in less risks and complications than the procedures using other lasers or mechanical devices. However, it is noted that the cavities 502 can be formed by any manner or device desired.

As shown in FIGS. 22-24, cavities 502 can form various configurations or patterns. For example, the cavities can form a substantially circular pattern (FIG. 22), a substantially ring-shaped pattern (FIG. 23), or a pattern that is offset from the main optical axis (FIG. 24). Each specific configuration is particularly useful for correcting a specific vision problem in the eye. For example, a substantially circular pattern facilitates correction of myopia and hyperopia, a substantially ringed shaped pattern facilitates correction of presbyopia and a pattern offset from the main optical axis facilitates correction of astigmatism. It is noted that these patterns and configurations are for exemplary purposes only and the cavities can be formed in any suitable configuration for correcting myopia, hyperopia and/or astigmatism or any other refractive error in the eye.

Figure 25:
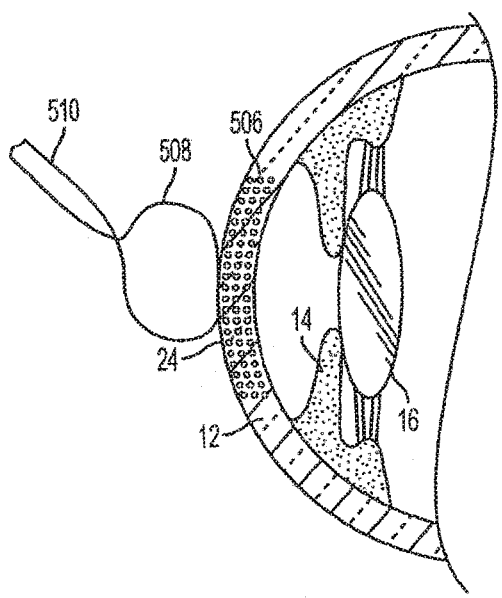
FIG. 25 is a side elevational view in cross section of the eye of FIG. 21 with a device applying a photosensitizer to the surface of the cornea.

As shown in FIG. 25 a photosensitizer or an ultraviolet absorbing compound 508 can be applied to the surface of the cornea 24 using a device or applicator 510 or any other suitable method or device. Additionally, the cross linker (i.e., the photosensitizer) can be applied also to a cross linkable material such as a corneal inlay made out of collagen or other organic, synthetic or semisynthetic material. The material can then be cross linked after the reshaping device is applied. The photosensitizer can be applied to the entire cornea or merely to specific areas and can absorb ultraviolet or near ultraviolet radiation to help facilitate or create cross-linking of collagen and hold the corneal structure into the new reformed shape. A suitable material for photosensitizing the cornea is riboflavin. Additionally, photosensitizer 508 is preferably a liquid or gel that is capable of initiating or catalyzing the energy from the laser 500; however, the photosensitizer can be any suitable substance or have any suitable consistency. Furthermore, the initiator does not necessarily need to be a photosensitizer and can be any suitable substance that facilitates formation of the cavities or reduces the heat and/or energy required to form the cavities 502.

Figure 26:
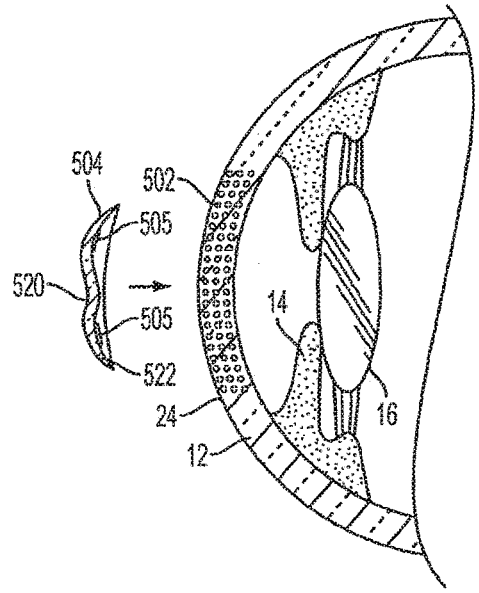
FIG. 26 is a side elevational view in cross section of the eye of FIG. 25 with a reshaping device proximate to the external surface of the cornea.
Figure 27:
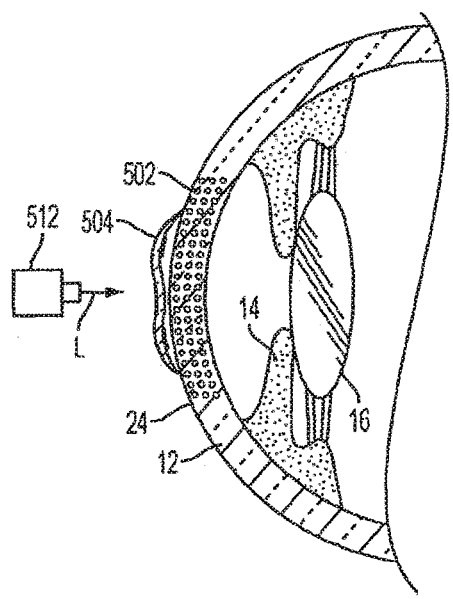
FIG. 27 is a side elevational view in cross section of the eye of FIG. 26 with the reshaping device immediately adjacent the external corneal surface and a laser heating the cornea.

Once the photosensitizer is applied and allowed to spread through or penetrate to the corneal stroma (or other desired portion of the eye), lens or reshaping device 504 is positioned immediately adjacent the external corneal surface, as shown in FIGS. 26 and 27. Reshaping device second surface 522 which has a predetermined curvature is preferably positioned immediately adjacent the external surface of the cornea, overlying all or substantially all of the cavities 502; however, it is noted that it is not necessary for the reshaping device to overlie all or substantially all of the cavities 502 and can overlie only a portion of the cavities 502, if desired or on the exposed surface of the cornea. The reshaping device 504 is substantially similar to the embodiments described above and any description thereof is applicable to the present embodiment, including the use of thermal couples 505.

Figure 28:
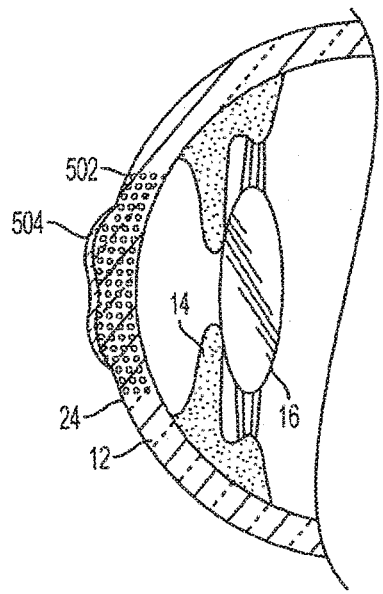
FIG. 28 is a side elevational view in cross section of the eye of FIG. 27 showing the cornea reshaped to conform to the predetermined shape of the reshaping device.

As shown in FIG. 28, laser or light emitting device 512 is aimed and fired at the corneal stroma, at or approximately at the portion of the cornea in which the cavities 502 are formed. Laser 512 can be the same laser, or a substantially similar laser, as laser 500, it can be any device capable of emitting ultraviolet light or near ultraviolet red radiation or laser 512 can be any suitable laser or light emitter. The laser beam L (preferably combined with the reaction from photosensitizer 508) then heats the corneal stroma to above body temperature and below a temperature at which coagulation occurs, preferably at about 60.degree. C., and preferably to between about 45.degree. C.–50.degree. C. The preferred temperatures allow or facilitate cross-linking of the collagen cells in the eye, so that the cornea can be reshaped more easily. As with the embodiments described above, the temperature can be controlled using the thermal couples and a suitable computer control system or manually. The light emitting device can also cross link the cornea without heat formation and without prior cavity formation.

Additionally, it is noted that the laser can heat the reshaping device, which in turn heats the cornea, or the cornea can be heated in any manner described herein.

By heating the corneal stroma to about or below 60.degree. C., the molecules of the cornea are loosened, and the cornea is cross linked, in a manner substantially similar to that described above. However, the corneal temperature is maintained at or below 60.degree. C., and therefore, protein denaturation does not occur as with conventional thermal coagulation. Since the heated portion of the cornea is now cross linked, the cornea reforms and is molded to take the shape of the inner surface of reshaping device 504, thereby forming the cornea into the reformed, corrected shape in an effort to provide the patient with 20/20 vision. The cornea can then cooled by applying cool or cold water, by applying air, by letting the reshaping device 504 cool through time or by simply removing the heated reshaping device or the heat from the reshaping device and using the ambient air temperature.

Figure 29:
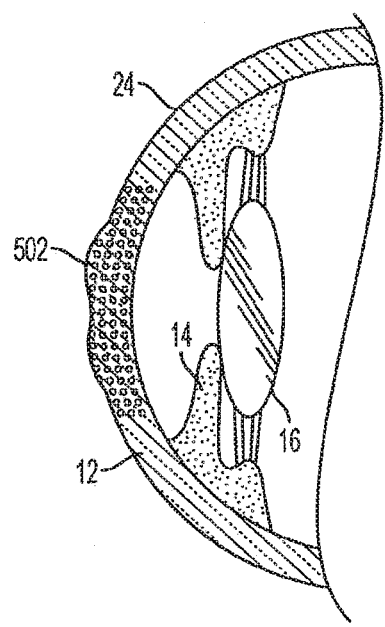
FIG. 29 is a side elevational view in cross section of the eye of FIG. 28 after the reshaping device has been removed.
Figure 30:
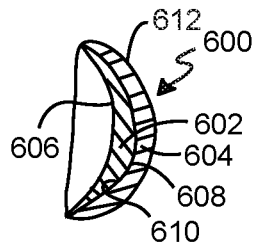
FIG. 30 is a side view in section of a device according to another embodiment of the present invention.
Figure 31:
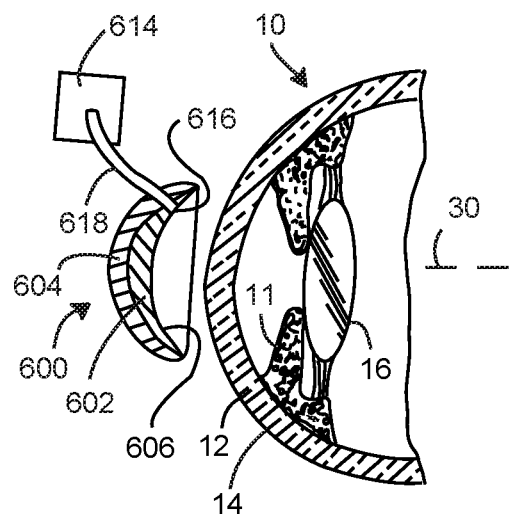
FIG. 31 is a side view in section of a device according to another embodiment of the present invention proximate to the surface of the cornea.
Figure 32:
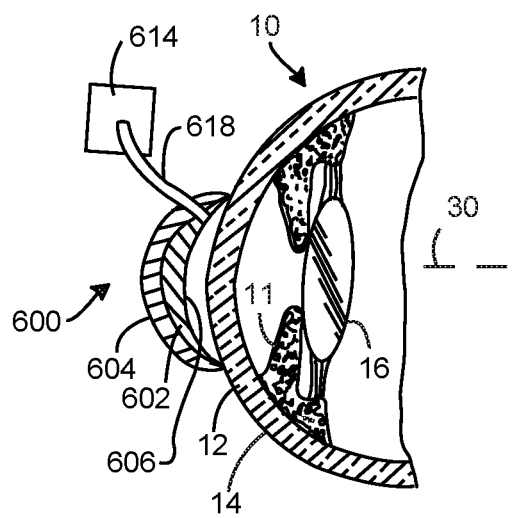
FIG. 32 is a side view in section of the device of FIG. 31 immediately adjacent the surface of the cornea.

Preferably, as the cornea cools, it is held by the reshaping device 504 to the preferred shape, which becomes its new permanent shape once the cornea is completely cooled and changes to its original substantially solid consistency, as shown in FIG. 29.

Preferably, the reshaping device 504 is transparent as described above, thus allowing the patient to see while the reshaping device is still on the external surface of the eye. In other words, as the cornea cools, the reshaping device 504 acts as a contact lens, if desired.

It is noted that reshaping device does not necessarily need to be applied to the external surface of the cornea and can the positioned directly on the Bowman's layer, directly on the corneal stroma or any other suitable portion of the cornea. This positioning can be achieved by forming a flap that would expose the desired portion of the internal structure of the cornea. As described herein the flap can be a Lasik type flap (i.e., attached to the cornea at the periphery—see FIG. 3), or it can be a flap that is attached at a central portion of the cornea (i.e., along the main optical axis), the flap can be completely removed, or the internal structure of the cornea can be exposed in any other suitable manner.

FIGS. 30-34 illustrate a device for reshaping the cornea 600 according to another embodiment of the present invention. Device 600 preferably has two portions, a first layer or portion 602 and a second layer or portion 604. However, it is noted that device 600 can be formed from one layer or portion (as described above) or multiple layers or portions, if desired.

First portion 602 has a first surface 606 that is adapted to be positioned adjacent a surface of the cornea and a second surface 608. First portion is preferably formed form a ceramic material or a polymer or another suitable material, such that the cornea of the eye is insulated from direct contact with second portion 604. Such insulation can reduce the risk of damaging, burning and/or scarring of the cornea.

Second portion 604 is preferably formed of a heat or electrically conducting material, such as metal or any material described above or any other suitable material. Portion 604 has a first surface 610 positioned substantially adjacent second surface of first portion 602 and a second surface 612 generally exposed and facing away from the patient.

The first and second portions generally have substantially the same shape and approximate thickness and second portion 604 preferably overlies first portion 602. Preferably, both the first and second portions are substantially circular or substantially ring-shaped but can be any suitable size or configuration to change the refractive properties of the eye in any desired manner or any suitable shape, In other words, the configuration of device 600 can be any suitable configuration to alter the refractive properties of the eye and correct for myopia, hyperopia, presbyopia, astigmatism or any other disorder.

The device shape can be substantially circular, substantially ring shaped, having an arcuate configuration (spanning from about 1 degree to about or less than 360 degrees) or any other configuration that could be positioned on a surface of the cornea to alter the shape thereof. Furthermore, the second portion does not necessarily need to overlie the second portion and each portion can be orientated relative to each other in any suitable or desired manner.

The first surface 606 of first portion 602 preferably has a predetermined shape to facilitate alteration of the cornea. For example, the surface can be substantially flat or have a curvature or radius that is greater than the curvature of the cornea to correct for myopic error, the surface can have a curvature that is greater than the cornea to correct for hyperopic error or the surface can be toric to correct astigmatism. The overall shape of the heated portion or the device itself can be substantially ring-shaped to correct hyperopia or presbyopia. Preferably, the substantially ring-shaped device has an opening of about 3 mm to about 8 mm, but can have any suitably sized opening.

As described herein, device 600 can be formed from any suitable material and be heated in any suitable manner. For example, device 600 can be heated using a heating source and electrical wires, heated water, a wireless device, such as a laser, or any other suitable device or mechanism. Additionally, the cornea can be heated while device 600 is positioned thereon or both the cornea and the device can be heated simultaneously. Generally, when heating the cornea in this manner, it is heated with a laser and the device is substantially transparent; however, the cornea and/or device 600 can be heated in any suitable manner.

Furthermore, the cornea can be irradiated with a laser of a specific wavelength (e.g., 375-400 nm or higher up to 3 microns or any other suitable wavelength) that will create cross linking in the cornea to facilitate alteration of the cornea. The cornea can also be altered using any type of suitable laser wavelength and heating, as described herein. The light can be circular, semicircular doughnut shaped or any other shape applied to the cornea for cross linking with or without a cross linker.

In one embodiment, the heating device can have portions thereof heated, while the remainder of the device is not heated. For example, the device can be substantially circular and all of the device, the outer periphery of the device, the center portion of the device, or any suitable portion of the device can be heated. Such selective heating allows specific portions of the device to be heated, thus transferring the heat to only select areas of the cornea to alter the refractive properties of the eye in a specific predetermined manner.

For example, a laser can be aimed and fired at only a portion of the device, the device can be wired such that electrical current can be applied to specific portions thereof, or specific portions of the device can be heated in other suitable wireless manners or in any desired manner. The heating of the cornea cross links the cornea and allows the overall shape of the cornea to be altered, as described herein.

Generally, pressure is applied to the device facilitating change of the surface of the cornea. Pressure can be applied by hand or by a tool. The pressure can be applied automatically by a means or device configured or programmed to apply a predetermined amount of suitable pressure.

Figure 33:
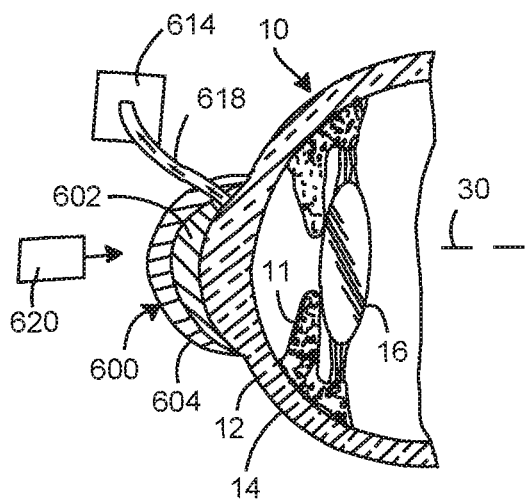
FIG. 33 is a side view in section of the device of FIG. 32 with a suction device holding the cornea to the internal shape of the device and a laser irradiating the reshaping device to cross link the cornea.
Figure 34:
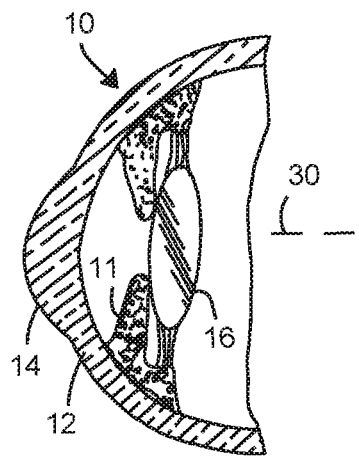
FIG. 34 a side view in section of the eye of FIG. 33 with the device removed and the cornea maintaining its reformed shape.

As shown in FIGS. 31-34, facilitating corneal change can also be achieved by using device 614 to form a vacuum between surface 606 of the device and the surface 14 of the cornea 12. For example, a small opening 616 can be formed from the second surface of the second portion of the device to the first surface of the first portion of the device. A tube 618 coupled to the device 614 for creating the suction can be coupled (or permanently affixed) to the passage, such that a vacuum or a reduced area of pressure is formed between the device 600 and cornea. Thus the cornea conforms to the predetermined shape of the first surface of the first portion of the device, as shown in FIG. 33. Simultaneously or substantially simultaneously, a laser 620 (or any other heating device described herein) heats a portion of the device 600 to facilitate altering the surface of the cornea as described above. Once the device is removed the cornea remains in the desired configuration, as shown in FIG. 34.

Suction can also be applied to the cornea using a device similar to the device in a microkeratome that creates suction to facilitate forming a LASIK style flap. A portion of the cornea can have suction applied thereto, and the mold device can be simultaneously applied to this portion or another portion of the cornea.

Furthermore, this method and device can be used in a substantially similar manner to the methods described above, the description of those methods along with the reference numerals used therein apply to this method. For example, the embodiment of FIG. 30 can be used with or without a laser forming cavities, with or without a photosensitizer, such as riboflavin, under a flap or on the surface of the cornea or any of the other methods and devices described above. Generally, the wavelength that activates the photo sensitizer is different than the wavelength to cross link the cornea; however, the any suitable wavelength can be used for either or both of the cross linking and activation of the photosensitizer.

7. Example

Figure 35:
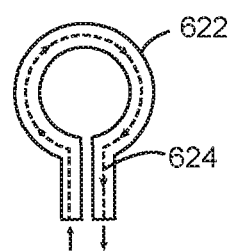
FIG. 35 is a top view of another embodiment of the present invention.

The herein described invention was performed on ten (10) eyes received from the eye bank. The device used was a copper tube 622 (FIG. 35) having a diameter of about 0.8 mm. The tube was shaped generally into a circle and positioned adjacent the external surface of the cornea. The tube can be shape as shown in FIG. 35, as a complete unitary circle with an entrance and an exit tube positioned in any suitable position relative to each other or the circle, be shaped in an arc having spanning less than 360 degrees or in any other suitable manner. Heated water 624 was passed through the tube at approximately 55 degrees Celsius. The tube made a substantially permanent indentation in the cornea, thus increasing the curvature thereof. No clouding of the cornea, damage to the corneal structure or cell death was observed and the indentation or curvature change was found to be stable.

The preferred temperature range is above body temperature and below 60 degrees C., and more preferably between about 47 degrees C. and 55 degrees C. Preferably, the cornea is heated for about 4 minutes to about 7 minutes, but can be heated to any suitable temperature for any suitable time period. Higher temperature generally requires less time of application of the device.

The amount of correction of presbyopia can be altered by changing the cross sectional diameter of the tube. For example, the smaller the diameter the less the correction and the larger the diameter the greater the correction of presbyopia. Preferably the diameter of the tube is between about 0.5 mm and 1.5 mm, but can be any suitable diameter.

In another embodiment, tube 622 or device 600 can be formed from glass of another transparent or translucent material and laser light can be transmitted through the tube to cross link the cornea (e.g., fiber optics).

Any of the above described devices can be heated themselves to alter the cornea, can work in conjunction with a device that heats the cornea directly or both the device and the cornea can be heated. Additionally, both a laser that irradiates the cornea with a cross linking wavelength and heating the cornea can be used simultaneously or in succession or any combination of these procedures, including the use of a photosensitizer can be used.

In another embodiment, cross linking of the collagen of the cornea and shrinkage or controlled altering of the cornea can be achieved with a cross linker or cross linking substance (e.g. Riboflavin). Preferably, the cross linker has between about 0.1% Riboflavin to about 100% Riboflavin or any specific range therein. This procedure is preferable performed using a device or means for emitting ultraviolet rays at the cornea. The modification or alteration of the cornea is then performed using a mold or device that has a predetermined configuration as described above.

The procedure using the cross linking substance can be used with the controlled heat methods described above, with ultraviolet rays or both or neither. Additionally, this procedure can be used to correct any and all refractive errors. For example, this method can be used to correct myopia, hyperopia, astigmatism, presbyopia and/or any other error.

The chemical cross linker (i.e., using a cross linking substance) can be performed before, simultaneous or after heat cross linking, if heat is used. Although not necessary, using both heat and the cross linking substance, will allow each to work synergistically with the other and reduce the time and temperature of cross linking needed.

When undertaking the procedure, the Photosensitizes or cross linkers can be applied to the corneal epithelium or the epithelium can be removed or the cross linkers can be applied to any exposed portion of the eye, such as the Bowman's Layer or the stroma. For example, a LASIK style flap or an epithelial style flap can be formed and the cross linker can be applied thereto. In is noted that a flap does not need to be formed and a portion of the cornea can be exposed in any desired manner.

The ultraviolet radiation or rays (when applied) are preferably between about 370 nanometers and about 380 nanometers. The radiation is preferably about 3 mW or more as needed and emanates from a device at about 3 cm distance from the cornea for about 30 minutes or less. However, the ultraviolet radiation can be applied at any suitable distance, time or wavelength.

Preferably the device for reshaping the eye has any suitable configuration, as described above, for altering or correcting refractive error. Preferably, the device is positioned on the exterior or the eye (i.e., on the epithelial layer). However, as with the cross linking substance, the device can be positioned on any exposed surface of the cornea, such as the Bowman's Layer or the stromal layer. Each of these layers or any other suitable layer of the cornea can be exposed using a pocket, flap, ablation or by removing portions of the cornea or in any suitable manner.

By virtue of the predetermined configuration of the device, the device alters the shape of the cornea, thus correcting the refractive error. The device can be preformed to correct any known refractive problem or alter the refractive properties of the cornea in any desired manner.

If desired, a means for applying pressure can be used to apply pressure to the device and thus help facilitate the altering of the corneal surface. The means can be any suitable portion of the person performing the procedure or any suitable tool than could attach or merely abut the outer surface of the device.

Preferably a control system, such as a computer, monitors and controls each of the aspects of the system, including but not limited to applying heat, ultraviolet radiation, applying the cross linker, and applying pressure to the device; however, it is noted that it is not necessary for a computer control system to monitor and control each of these systems and steps and can monitor and/or control any number of the systems and steps. Further, it is not necessary to even use a computer control system.

This procedure or any of the procedures described herein can be used alone, or in conjunction with, simultaneously with, before or after any other procedure, method or device that would alter, correct or enhance the refractive properties of the eye.

Implantation of polymeric material is a common procedure to replace or improve the function of various organs. It is known that all implants are encapsulated by fibrous or fibrovascular tissue. Though this encapsulation can be beneficial, often it can lead to complications of gradual expulsion of the implants or produce considerable cloudiness of the surrounding proliferating fibrous tissue, e.g., in the cornea.

To our knowledge except for the use of immunosuppressive agents which have significant side effects no other method is available to prevent or reduce the intensity of this process.

While this application describes the use of a new methodology to reduce the chance of encapsulation in an animal cornea when an organic or synthetic material is implanted the technology is not limited to this area it can be applied also to glaucoma shunt, cosmetically or functionally used implants or prevention of vessel restenosis after stent placement.

FIGS. 40a-e illustrate another embodiment of the present invention. In particular, the present embodiment includes cross linking tissue, specifically collagen and other proteins surrounding an implant 800, to make the tissue less vulnerable to enzymatic degradation and change; thereby making the cornea 802 less likely to be invaded by various migrating cells, such as leucocytes, macrophages, fibroblasts and blood vessels endothelial cells. These cells subsequently build the basis for gray-whitish discoloration along with vascular components seen in encapsulated implants.

Figure 36A:
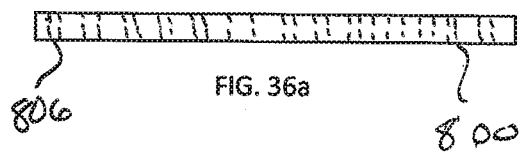
FIG. 36a is a side elevational view of an implant with holes provided therein.
Figure 36B:
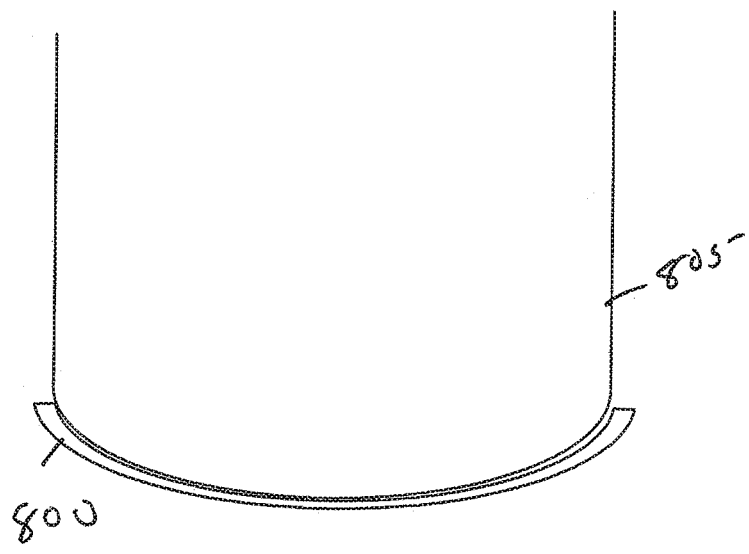
FIG. 36b illustrates a tool being used to shape a semi-circular implant.
Figure 36C:
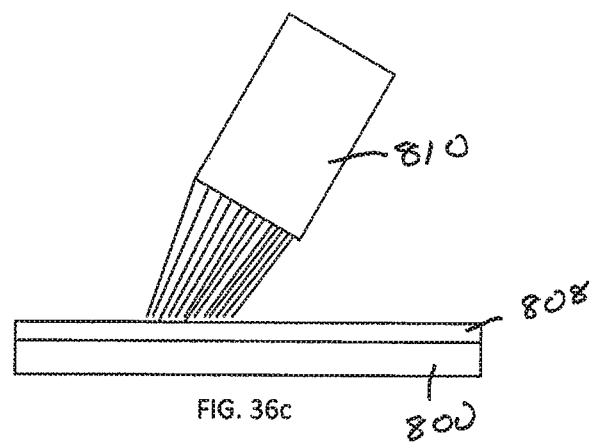
FIG. 36c illustrates a polymeric material being painted on an implant using a brush.
Figure 36D:
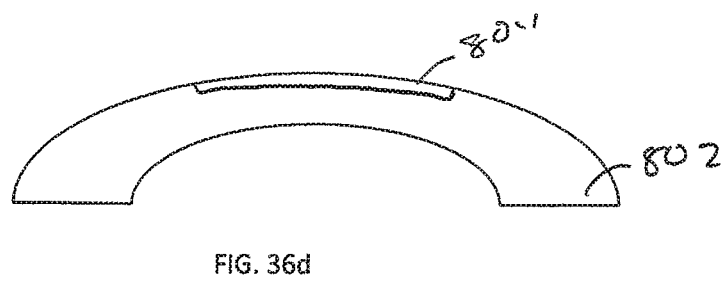
FIG. 36d illustrates a corneal flap formed in the cornea of an eye.
Figure 36E:
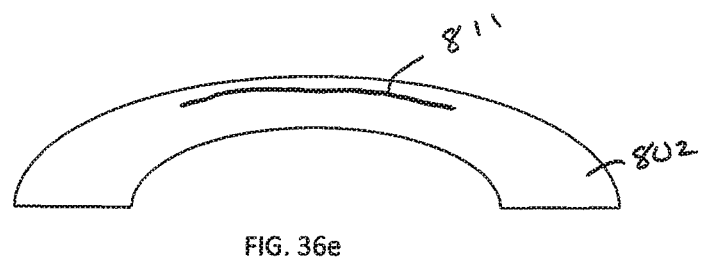
FIG. 36e illustrates an incision formed in the cornea of an eye.
Figure 36F:
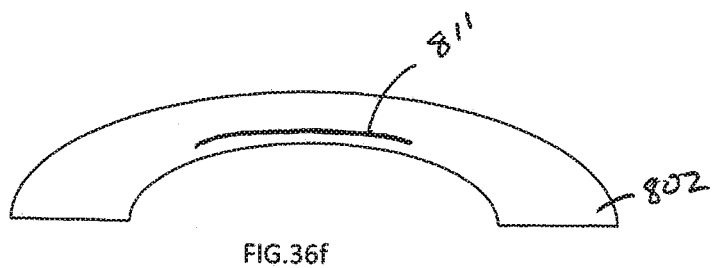
FIG. 36f illustrates another incision formed in the cornea of an eye, the incision depicted in this figure being disposed posteriorly from the incision of FIG. 36e.
Figure 36G:
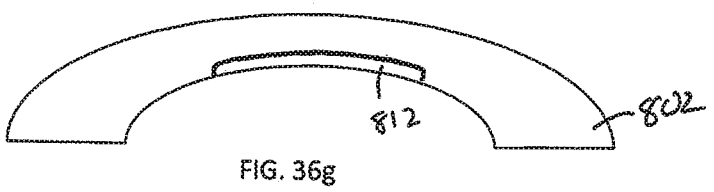
FIG. 36g illustrates an anterior chamber formed in the cornea of an eye.
Figure 36H:
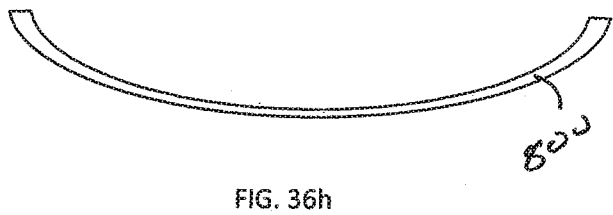
FIG. 36h illustrates the semi-circular implant formed by the tool depicted in FIG. 36b.
Figure 37A:
FIG. 37a illustrates an incision formed in the cornea of an eye.
Figure 37B:
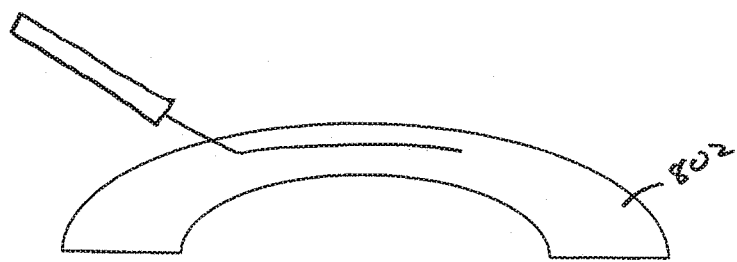
FIG. 37b illustrates the separation of the tissue bounding the incision so as to create an internal pocket in the cornea.
Figure 37C:
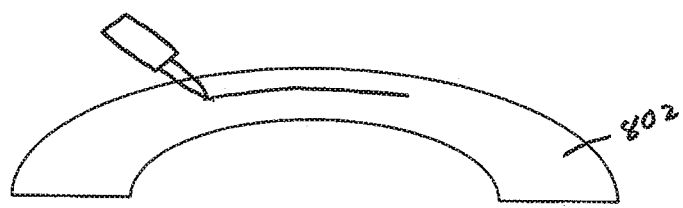
FIG. 37c illustrates the injection of a liquid polymer into the internal pocket of the cornea.
Figure 37D:
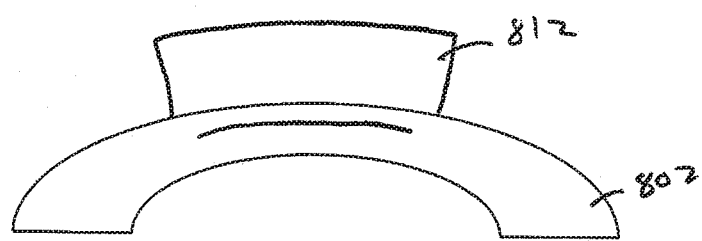
FIG. 37d illustrates the compression of the front surface of the cornea using a contact lens or sclera lens, followed by subsequent cross-linking.

The implant 800 is generally implanted under a corneal flap 804 (e.g., see FIGS. 38c-38f). Thus, the implant may be surrounded completely by the corneal tissue or partially exposed out to a side surface or to the inside limited by the anterior chamber of the eye. The implant can be an organic or synthetic, hydrophilic, hydrophobic polymer, and can have minute (<2 micron) holes 806 therein for transport of fluid thereacross (see FIG. 36a). The implant 800 can have a thickness of <1-500 micron or >, and can have a cross linking substance in it. The implant can be shaped into a predetermined configuration using a tool 805, as shown in FIGS. 36b and 36h.

FIGS. 37 and 38 show flap 804, which can be circular or any shape involving 20-360 degrees of the cornea. The flap diameter can be 2 mm-12 mm and the flap can have a thickness of 50 microns to >400 microns. To form the flap, a Micro-keratome or a Femto-second laser, etc. (before or after cross linking) can be used to create the incision in the cornea of any desired shape circular or doughnut or sectorial. The flap can be made in any portion of the cornea desired. For example, see FIGS. 36d-g in which the flap 804, or an incision 811 can be made in the stroma, the epithelial, near the surface of the cornea, or near the anterior chamber. Moreover, as illustrated in FIGS. 36d-g, the epithelial, at the surface of the cornea or at the anterior chamber (see 812) can be removed.

Polymeric material 808, such as gel nail, etc., can be injected or painted under the corneal flap (e.g., using brush 810—see FIG. 38d), as a very thin layer of the cornea is compressed from outside using a contact lens or sclera lens 812 having a desired inside curvature to correct the refractive error of the cornea and subsequently cross linked. During the cross linking this semi-liquid film of polymer spreads uniformly when compressed from outside with contact lens 812 and creates the desired curvature which remains stable after the cross linking process is finished (as is done with the nail gel). This can also serve as a mechanical support to a weak cornea, etc. (when the implant is hardened during the cross linking with UV light) as in corneal ectasia seen in keratoconus patients or after LASIK surgery, etc. It is important to note that the polymer 808 per se (i.e., by itself) will not necessarily have a refractive surface and cannot correct refractive errors of the eye unless it is shaped by the compression effect exerted on the cornea by a specific contact lens 812 which has a specific curvature to correct the refractive error after the implant is hardened. If the polymer 808 and the cornea 802 were not cross linked in this position one would not achieve any predictable corrective or supportive effect.

Figure 38A:
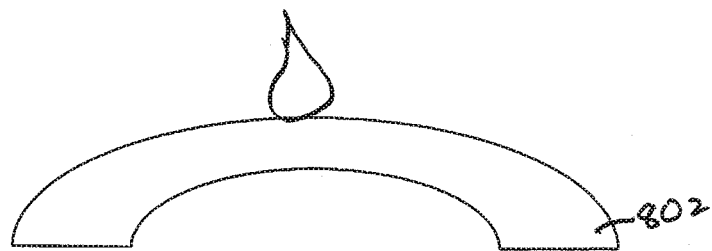
FIG. 38a illustrates the application of a photosensitizer (e.g., riboflavin) to the cornea of an eye.
Figure 38B:
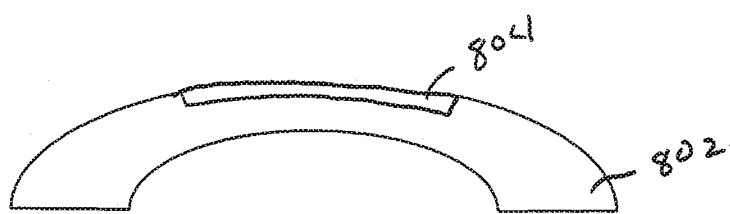
FIG. 38b illustrates the formation of a corneal flap formed in the cornea of the eye.
Figure 38C:
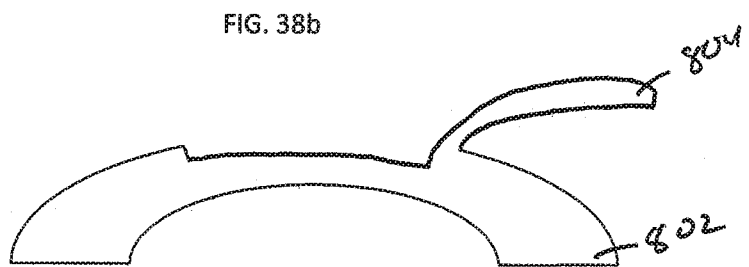
FIG. 38c illustrates the raising of the corneal flap.
Figure 38D:
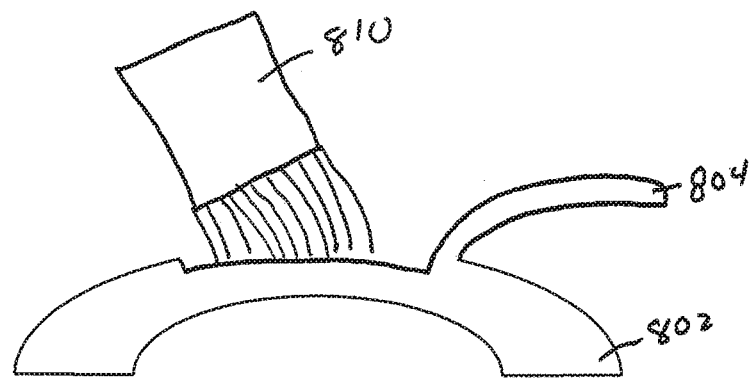
FIG. 38d illustrates a polymeric material being painted on the exposed corneal tissue underneath the flap using a brush.
Figure 38E:
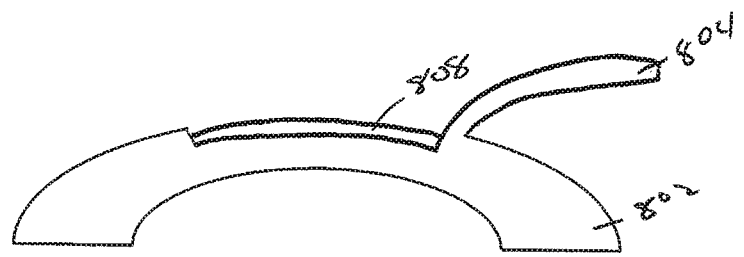
FIG. 38e illustrates the polymeric material covering the exposed corneal tissue underneath the flap.
Figure 38F:
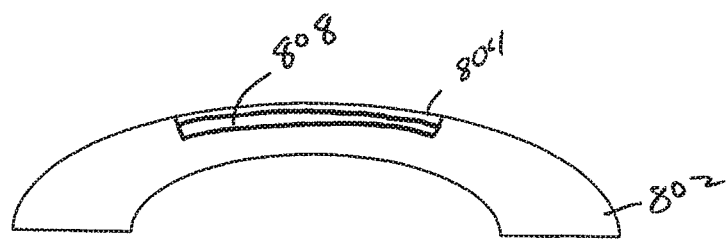
FIG. 38f illustrates the replacing of the corneal flap so as to cover the polymeric material painted on the cornea of the eye.
Figure 38G:
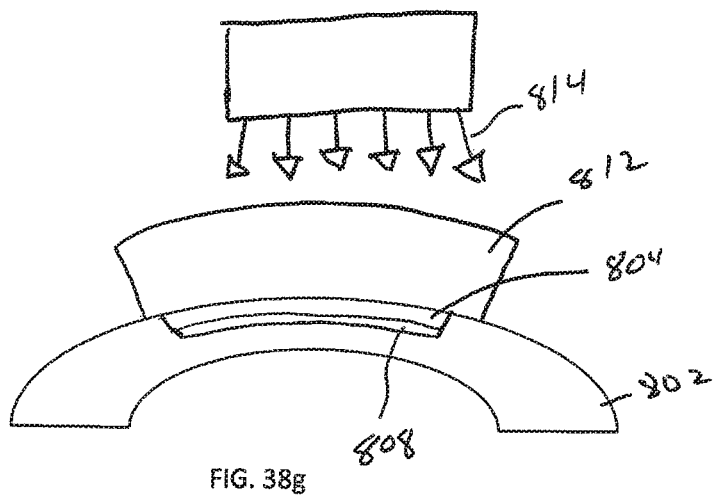
FIG. 38g illustrates the compression of the front surface of the cornea using a contact lens or sclera lens and cross-linking of the implant using radiation (e.g., ultraviolet radiation)
Figure 39A:
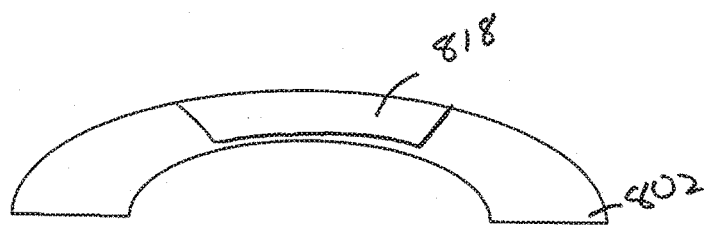
FIG. 39a illustrates the removal of corneal tissue from the front surface of the cornea of an eye so that an implant is capable of being inserted in the cornea.
Figure 39B:
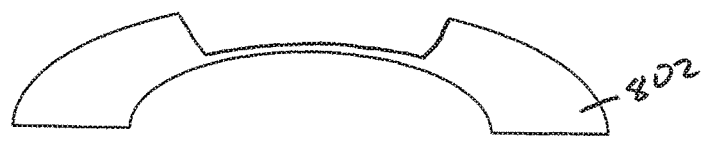
FIG. 39b illustrates the cornea of the eye after the corneal tissue has been removed from the front surface thereof.
Figure 39C:
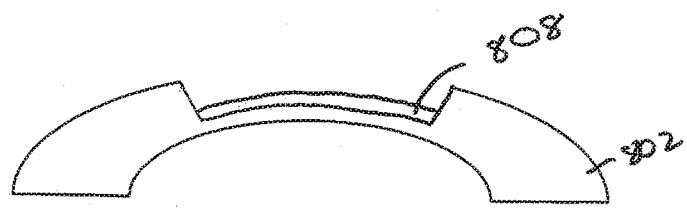
FIG. 39c illustrates the insertion of an implant coated with a photosensitizer into the recess in the cornea of the eye that was created by the removal of the corneal tissue.
Figure 39D:
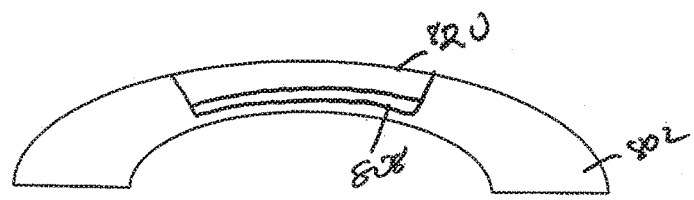
FIG. 39d illustrates the replacement of corneal tissue (e.g., donor tissue) back on the front surface of the cornea of the eye so that the implant is covered thereby.
Figure 39E:
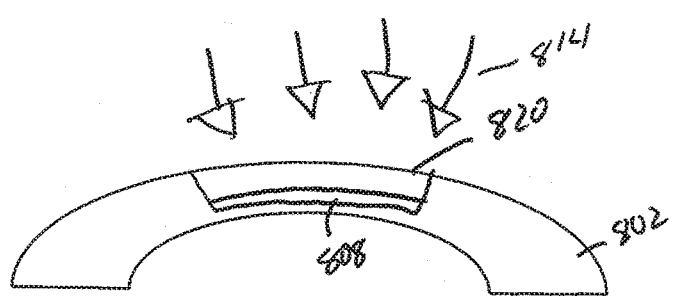
FIG. 39e illustrates the irradiation of the implant and the cornea of the eye from outside the eye.
Figure 39F:
FIG. 39f illustrates the cornea of the eye with the implant disposed therein after it has been irradiated.
Figure 40A:
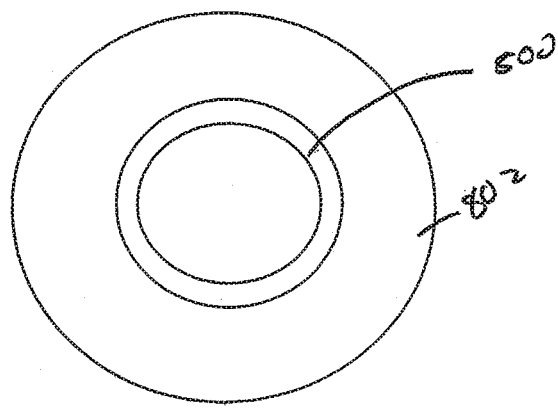
FIG. 40a illustrates an annular-shaped corneal implant.
Figure 40B:
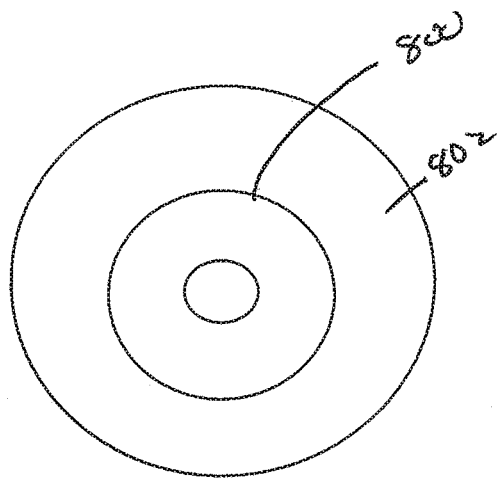
FIG. 40b illustrates a donut-shaped corneal implant.
Figure 40C:
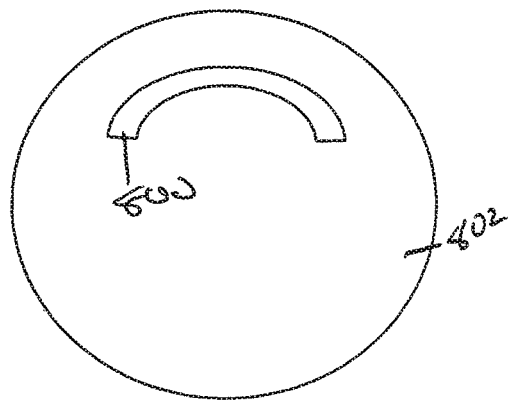
FIG. 40c illustrates a semi-circular corneal implant.
Figure 40D:
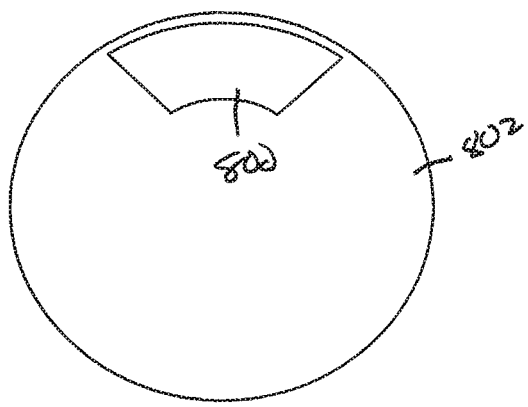
FIG. 40d illustrates a sectorially-shaped corneal implant.
Figure 40E:
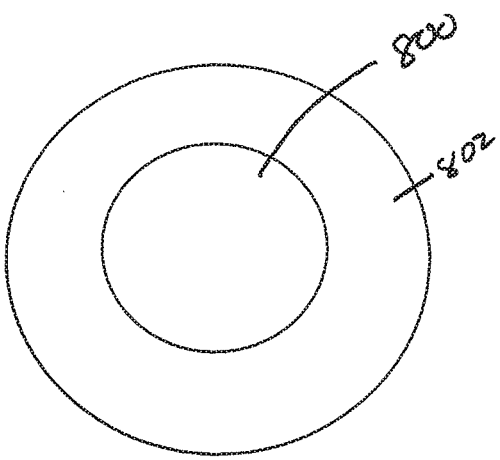
FIG. 40e illustrates a circular corneal implant.

Cross linking (see FIG. 38a) is achieved by various processes, such as using Riboflavin plus subsequent radiation with near UV light 814 to activate cross linkers (see FIGS. 38g and 39e). Other cross linking methods include radiation, heat, gluthar-aldehyde and other solutions, such as low carbon sugars, etc. The tissue in which the implant is placed can be cross linked ahead of implantation or after implantation. The implant can have a cross linker coated or incorporated in it which can leak in the surrounding tissue then subjected to radiation. In one embodiment, the cross linking includes some tissue outside the perimeter of the implant. Although, in another alternative embodiment, the cross linking only includes the tissue surrounding the perimeter of the implant.

Cross linking of the corneal collagen can be achieved with a cross linker or cross linking substance (e.g. Riboflavin). Preferably, the cross linker has between about 0.1% Riboflavin to about 100% Riboflavin or any specific range therein. This procedure is preferably performed using a device or means for emitting ultraviolet rays at the cornea.

When undertaking the procedure, the photosensitizers or cross linkers can be applied to the corneal epithelium or the epithelium can be removed or the cross linkers can be applied to any exposed portion of the eye, such as the Bowman's Layer or the stroma. For example, a corneal flap or an epithelial style flap can be formed and the cross linker can be applied thereto.

The ultraviolet radiation or rays (when applied) are preferably between about 370 nanometers and about 380 nanometers. The radiation is preferably about 3 mW or more as needed and emanates from a device positioned at about 3 cm from the cornea for about 30 minutes or less. However, the ultraviolet radiation can be applied at any suitable distance, time or wavelength. The standard way of cross linking the cornea does not provide a complete stability, since the cornea does not change the refractive power of the cornea significantly.

Attempts to reshape the cornea by external means during the cross linking the device for reshaping the eye have been successful. Although the use of corneal inlays has been described, these have been often fraught with encapsulation and corneal cloudiness. These implants have tried to change the curvature of the front surface of the cornea by acting like an optical lens having a surface with defined surface and curvature (convex or concave etc.) to create the desired change on the surface of the cornea. This implant does not provide any substantial stability to the cornea and can also be rejected by the corneal tissue. Therefore, there is a need to provide a means of providing internal stability to the cornea using a thin flat membrane-like implant that has little or no refractive surface but can be significantly hardened after cross linking without its surface swelling (increase in thickness or decrease in thickness). However, a hardness can be achieved that is needed after cross linking and a new curvature can be adopted before the cornea is cross linked. If pressed on during the hardening process, the thin flat membrane-like implant can assume a refractive curvature (similarly to gel nail which is painted over the nail that assumes the nail curvature when it hardens). This new implant can be applied on the tissue or under the tissue (e.g., a corneal flap) like a paint over or can be implanted as a flexible transparent membrane inside the tissue then hardened or cross linked with UV radiation (FIG. 36a-h). The membrane can have a cross linker substance thereon to harden during the radiation. The membrane may have the same cross linker that is used for the tissue and the implant.

Initially, the implant has no curvature; however, the implant can change the refractive power of the cornea if it is pressed against a curved surface during the cross linking and hardens in that position. When the implant hardens, it provides a "back bone" for the cornea and prevents corneal ectasia. A cross linking substance is applied as described above to the exposed corneal stroma or under the corneal flap.

In another embodiment, shown in FIGS. 39a-f, if desired, and preferably after the implantation and cross linking, the remaining corneal thickness under 816 or over the implant 818 can be removed e.g. from the inside the anterior chamber through a small incision using an angulated, knife, scissors, or laser to cut the tissue which is subsequently removed with a fine forceps under viscoelastic material. This technique can create a clear window to outside world. Additionally, as shown in FIGS. 39e and f, the remaining cornea or a donor portion 820 from an eye bank can be positioned in the opening created by removal of the remaining corneal thickness.

8. Embodiments of FIGS. 41a-47f

It is known to one of ordinary skill in the art, that the normal corneal thickness is about 490-560 microns. Generally, thin corneas are found often in patients who have high myopia (i.e., near sightedness). Such thin corneas, i.e., having a thickness of <480 microns, are not candidates for modern refractive surgery using an excimer laser or any tissue removal for the correction of refractive errors. That is, ablation of these corneas affects biomechanics of the cornea, leading to outbulging of the cornea, which often requires a corneal transplant. Cross linking of the cornea has been recently advocated to correct the refractive problems of the eyes having these types of corneas (e.g., by the present inventor) for advanced corneal ectasia, such as in Keratoconous to stabilize the condition. However, no method exists to perform refractive surgery on thin corneas. The corneal ablation in these patients generally will lead to further thinning of the cornea, reduced stability of the cornea, and possible corneal perforation.

The present embodiment of this invention, as shown in FIGS. 41a-f is a method for correcting refractive error in patients with thin corneas, e.g., <500 microns thick. Except for glasses, contact lenses or implantation of a corrective lens inside the eye, there is no known method to correct the refractive errors of these types of patients.

This embodiment has the following advantages: 1) prevents corneal ectasia in eyes with thin cornea undergoing laser ablative surgery to correct refractive error of the eye; 2) reduces the sensation of burning of the cornea after surface ablation, since the corneal sensation is slightly reduced after initial corneal cross linking done in this procedure; and 3) reduces the corneal haze response to the laser ablation when the cornea is cross linked and after a period of healing laser ablation is performed. Moreover, a cross linked cornea does not respond to injury as strongly as the normal cornea does. This lack of response makes it also possible to perform ablation of the cornea in cases of high refractive error since a normal cornea would generally create haze after such procedure.

Generally, the present embodiment combines corneal cross linking with a refractive surgical procedure. More particularly, in one embodiment, the cornea is cross linked to stiffen the cornea prior correction of the refractive error followed by refractive surgery after the cornea is held, or in another embodiment, reversing the order by initially performing the refractive surgery followed by corneal cross linking within a predetermined period of time.

Figure 41A:
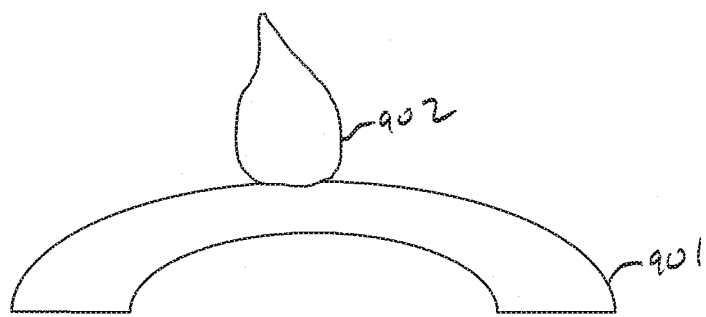
FIG. 41a illustrates the application of a photosensitizer (e.g., riboflavin) to the cornea of an eye.
Figure 41B:
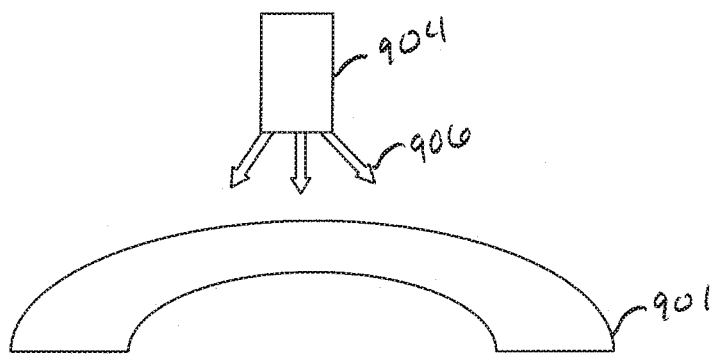
FIG. 41b illustrates the irradiation of the cornea of the eye from outside the eye using radiation (e.g., ultraviolet radiation)

In one embodiment, as shown in FIG. 41a, cross linking of the cornea 901 can be achieved by at least one of various processes, such as the use of a substance 902, such as Riboflavin, and subsequent radiation with a device 904, such as a laser, which emits near UV light so as to activate cross linkers (see FIG. 41b). Other cross linking methods include radiation, heat, microwave, gluthar-aldehyde and other solutions such as low carbon sugars, etc.

Preferably, the cross linker has between about 0.1% Riboflavin to about 100% Riboflavin or any other suitable range or specific percentage therein. In this embodiment, device or means 904 for emitting ultraviolet rays 906 is used, along with the position of its application. In another embodiment, the solution can be applied as a liquid suspension having nano particles of Riboflavin. Such an embodiment uses specific lenses for focusing the light.

When undertaking the procedure, the photosensitizers or cross linkers can be applied to the corneal epithelium or the epithelium can be removed or the cross linkers can be applied to any exposed portion of the eye, such as the Bowman's Layer or the stroma. For example, a corneal flap 907 (see FIGS. 41c and d) or an epithelial flap can be formed and the cross linker can be applied to the portion of the eye that has been exposed.

The ultraviolet radiation or rays (when applied) are preferably between about 370 nanometers and about 380 nanometers. The radiation is preferably about 3 mW or more as needed and emanates from device 904 at about 3 cm distance from the cornea for about 30 minutes or less. The time of the exposure can vary depending on the light intensity, focus, and the concentration of Riboflavin. However, the ultraviolet radiation can be applied at any suitable distance, time or wavelength. Preferably, cross linking the cornea does not significantly change the refractive power of the cornea; however, if desired, cross linking can change the refractive power of the cornea to any suitable degree.

Figure 41C:
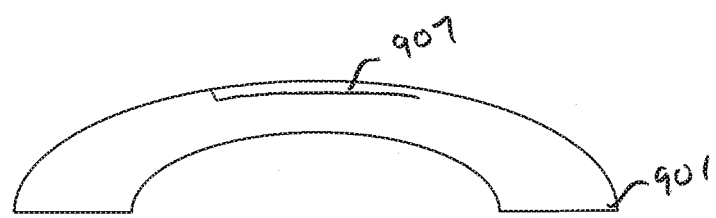
FIG. 41c illustrates the formation of a corneal flap in the cornea of the eye.
Figure 41D:
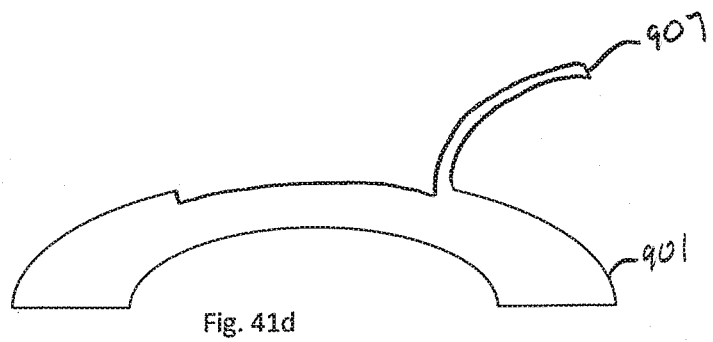
FIG. 41d illustrates the raising of the corneal flap.
Figure 41E:
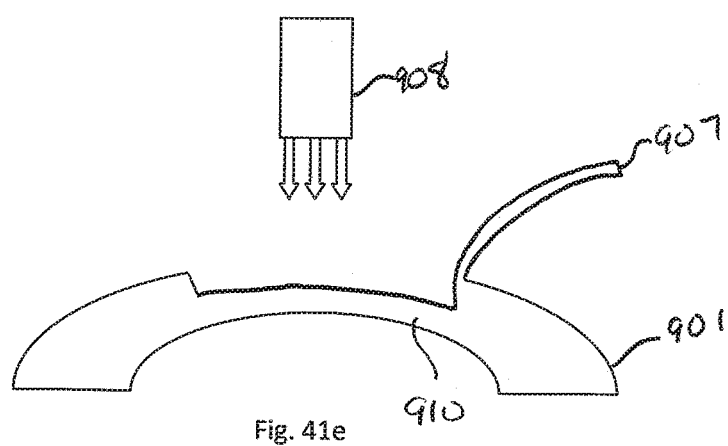
FIG. 41e illustrates the ablation of the exposed corneal tissue underneath the flap using a laser unit (e.g., an excimer laser)

After performing the corneal cross linking and waiting a reasonable time (e.g., 1-6 weeks or more or any suitable amount of time) for the cornea to recover, the cornea 901 can be altered by a laser unit 908, such as an excimer laser, as shown in FIG. 41e, or by other suitable methods. In one embodiment, the excimer laser ablates a portion of the cornea, such that a corneal portion 910 is thinner than prior to ablation. Such alteration changes the refractive properties of the cornea, thus enabling correction of vision in the eye.

Preferably, a predetermined period of waiting may allow for reduction or elimination of any photosensitizer which might still be present in the cornea after cross linking; however, the period of waiting can be any suitable period of waiting and is not necessary. Initially, prior to ablation, the refractive power of the eye is determined. This information is then transmitted to laser unit 908 to ablate the cross linked cornea. The ablation can be done intrastromally, as with LASIK (laser-assisted in situ keratomileusis), or on the surface of the cornea, as with PRK (Photorefractive keratectomy).

In particular, as shown in FIGS. 41c-e, a flap 907 (e.g., a stromal flap, an epithelial flap or any other suitable flap) can be formed in the cornea 901 using any known method, such as using a microkeratome (not shown). As shown in FIG. 41d, the flap 907 can then be moved so as to expose a portion of the cornea underlying the flap, such as the stroma surrounding the main optical axis of the eye, or any other suitable portion of the cornea. Preferably, the portion underlying the flap is an area at or surrounding the main optical axis; however, this portion can be any suitable portion of the cornea. Exposing the cornea in this manner enables excimer laser 908 to irradiate the cornea so as to ablate a portion thereof, as shown in FIG. 41e.

Figure 41F:
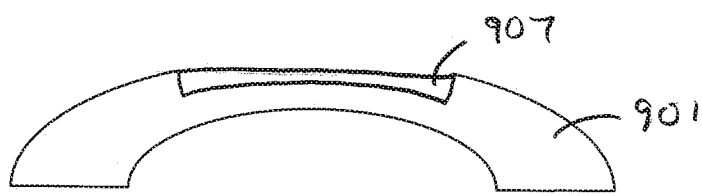
FIG. 41f illustrates the cornea of the eye after the corneal flap has been closed.

As shown in FIG. 41f, this procedure is effective for altering the curvature of the cornea, such that myopia, hyperopia and astigmatism or any other suitable vision problems can be corrected. Moreover, by performing the cross linker before or after ablation of the cornea (or other method altering the refractive properties of the eye) the cornea becomes stiffer, thus preventing corneal out bulging after laser ablation, since laser ablation makes a thin cornea even thinner. That is, the cross linked cornea facilitates resistance of the intraocular pressure, which pushes the cornea forward.

Additionally, post-operative medications such as anti-inflammatory agents, antibiotics etc., can be applied to the cornea.

One illustrative embodiment of a method of altering the refractive properties of an eye is shown in FIGS. 42a-42f. In general, the procedure illustrated in these figures involves forming a flap in the cornea of an eye, and then ablating the corneal tissue underneath the flap prior to the cross-linking of the tissue. Referring initially to the diagrammatic view of FIG. 42a, it can be seen that the eye undergoing ablation generally includes a cornea 1000 and an iris 1002.

Figure 42A:
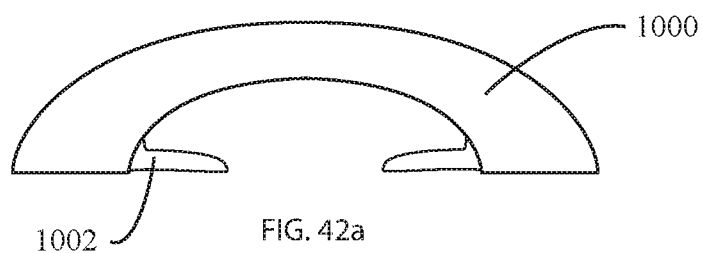
FIG. 42a is a partial side cross-sectional view of an eye prior to a procedure for altering the refractive properties being performed thereon, according to an embodiment of the invention.
Figure 42B:
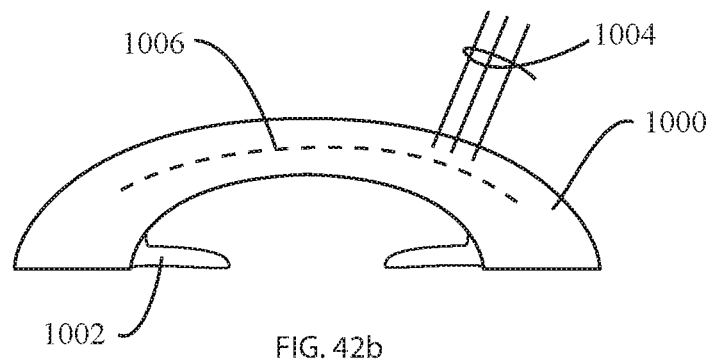
FIG. 42b is another partial side cross-sectional view of the eye of FIG. 42a illustrating the cutting of a flap therein.

In FIG. 42b, the cutting of a flap in the cornea 1000 of the eye is diagrammatically illustrated. In particular, as shown in the illustrative embodiment of FIG. 42b, an incision 1006 is made in the cornea 1000 of the eye using femtosecond laser 1004 (i.e., the incision 1006 is cut in the cornea 1000 using the laser beam(s) emitted from the femtosecond laser). In an alternative embodiment, the flap may be cut in the cornea 1000 using a mechanical keratome or a mechanical microkeratome. In the illustrated embodiment, the flap that is formed in the cornea 1000 may have a diameter between about 8.0 millimeters and about 11.0 millimeters, inclusive (or a diameter between 8.0 millimeters and 11.0 millimeters, inclusive). As such, in the illustrative embodiment, the flap has a diameter that is smaller than the overall corneal diameter.

Figure 42C:
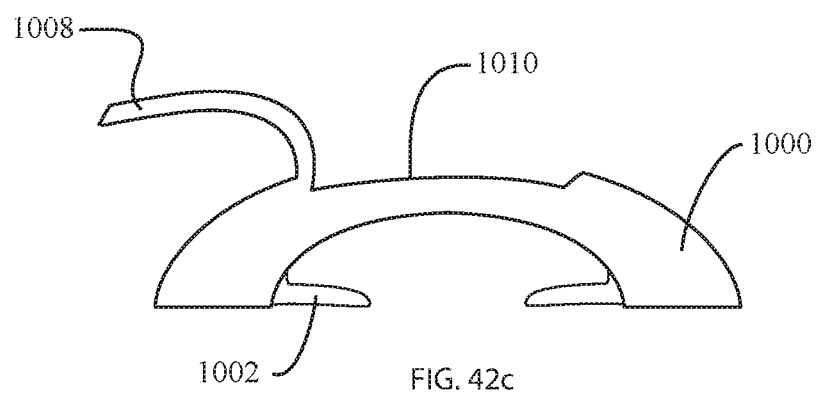
FIG. 42c is yet another partial side cross-sectional view of the eye of FIG. 42a illustrating the pivoting of the flap to expose the portion of the cornea underlying the flap.
Figure 42D:
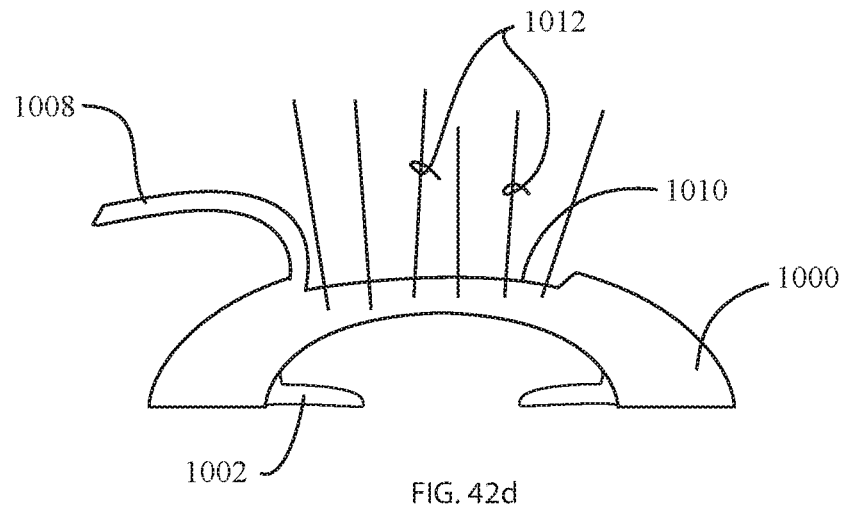
FIG. 42d is still another partial side cross-sectional view of the eye of FIG. 42a illustrating the ablation of the portion of the cornea underlying the flap so as to change the refractive properties of the eye.

Turning to FIG. 42c, it can be seen that, after the flap is cut using the femtosecond laser 1004, the corneal flap 1008 is pivoted or turned back so as to expose the portion 1010 of the cornea 1000 (i.e., the corneal stroma or stromal tissue) underlying the flap 1008. Then, referring to the illustrative embodiment of FIG. 42d, the exposed portion 1010 of the cornea 1000 underlying the flap 1008 is ablated using an excimer laser 1012 so as to change the refractive properties of the eye (i.e., the exposed corneal stroma is ablated using the laser beam(s) emitted from the excimer laser).

Figure 42E:
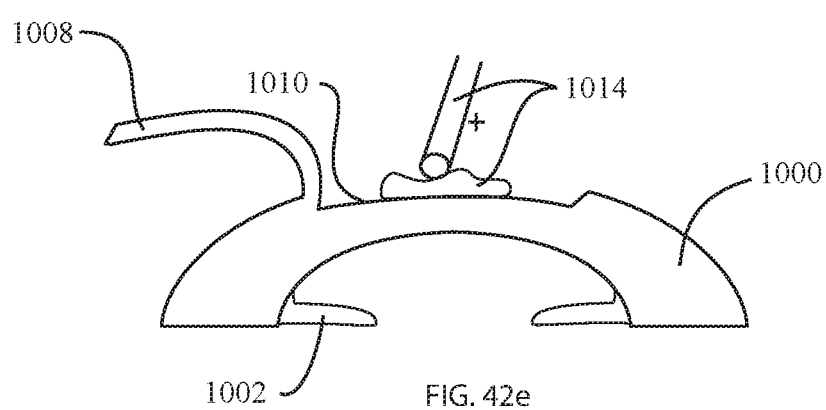
FIG. 42e is yet another partial side cross-sectional view of the eye of FIG. 42a illustrating the application of a photosensitizer to the ablated portion of the cornea underlying the flap.

After the exposed portion 1010 of the cornea 1000 underlying the flap 1008 has been ablated, a photosensitizer 1014 is applied to the ablated portion of the cornea 1000 underlying the flap 1008 (see FIG. 42e). The photosensitizer 1014 facilitates the cross-linking of the ablated portion of the cornea 1000 (i.e., the exposed corneal stroma that has been ablated). In one or more embodiments, the photosensitizer or cross-linker 1014 that is applied to the exposed corneal stroma comprises riboflavin, and/or a liquid suspension having nanoparticles of riboflavin disposed therein.

Preferably, the cross-linker 1014 has between about 0.1% riboflavin to about 100% riboflavin therein (or between 0.1% and 100% riboflavin therein). While riboflavin is used as a cross-linker of the collagen in the illustrated embodiment, it is to be understood that, in other embodiments, other cross-linking agents may be used alone, or in conjunction with the riboflavin.

Figure 42F:
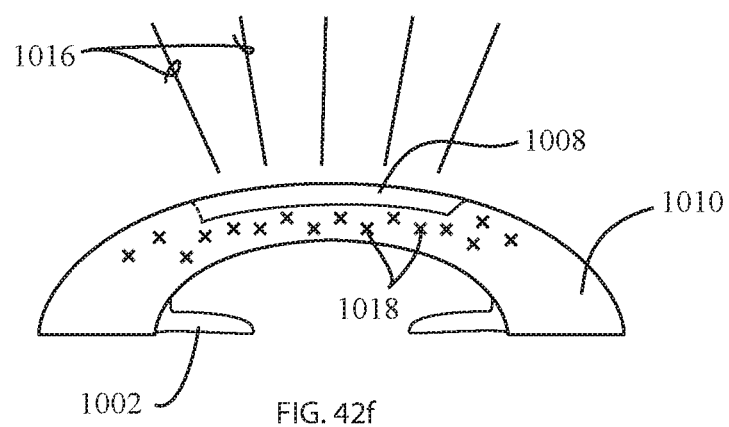
FIG. 42f is still another partial side cross-sectional view of the eye of FIG. 42a illustrating the irradiation of the cornea so as to activate cross-linkers in the ablated portion of the cornea after the flap has been replaced.

Next, turning to the illustrative embodiment of FIG. 42*f*, the flap 1008 is replaced over the ablated portion 1010 of the cornea 1000 (i.e., the flap 1008 is turned back to its position on the corneal stroma). Finally, shortly thereafter, the entire cornea 1000 is irradiated from the outside using ultraviolet (UV) radiation 1016 so as to activate cross-linkers in the ablated portion 1010 of the cornea 1000 and thereby stiffen the cornea 1000 and prevent corneal ectasia of the cornea 1000. In the illustrative embodiment, the ultraviolet light used to irradiate the cornea 1000 may have a wavelength between about 370 nanometers and about 380 nanometers (or between 370 nanometers and 380 nanometers). Also, in the illustrative embodiment, the corneal stroma inside the cornea 1000, which is exposed to the cross-linker 1014, is selectively cross-linked leaving the anterior part of the flap 1008 and the posterior part of the stroma uncross-linked. That is, in the illustrative embodiment, the cornea 1000 is irradiated such that only a predetermined anterior stromal portion 1018 of the cornea 1000 to which the photosensitizer was applied is cross-linked, thereby leaving an anterior portion of the flap 1008 and a posterior stromal portion of the cornea 1000 uncross-linked. The portion of the cornea 1000 without the cross-linker is not cross-linked when exposed to the UV radiation. In an alternative embodiment, the cornea 1000 may be irradiated using microwaves as an alternative to, or in addition to being irradiated using ultraviolet (UV) radiation.

In yet another embodiment, the cross-linking is done with ultraviolet (UV) radiation after closure of the corneal flap 1008 with a radiation diameter of only 1 to 2 millimeters (mm) beyond the implant. As such, the whole flap 1008 is not irradiated.

Another illustrative embodiment of a method of altering the refractive properties of an eye is shown in FIGS. 43*a*-43*d*. In general, the procedure illustrated in these figures involves forming a large pocket in the cornea of an eye, cross-linking the interior stroma, and then ablating the corneal tissue after the cross-linking has been performed. In this embodiment, no flap is formed in the cornea 1100 of the eye. Referring initially to the diagrammatic view of FIG. 43*a*, it can be seen that the eye undergoing ablation generally includes a cornea 1100, an iris 1102, and a lens 1104.

Figure 43A:
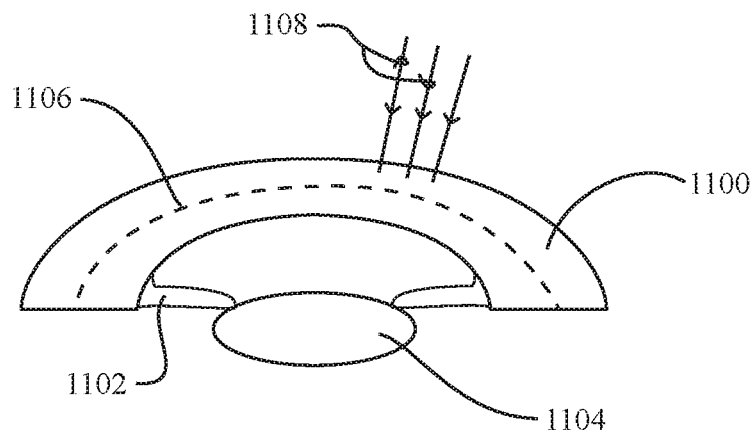
FIG. 43a is a partial side cross-sectional view of an eye on which a procedure for altering the refractive properties of the eye is to be performed, according to another embodiment of the invention, wherein the forming of a pocket in the eye is illustrated in this figure.

In FIG. 43*a*, the forming of a large corneal pocket 1106 in the cornea 1100 of the eye is diagrammatically illustrated. The formation of the large corneal pocket 1106 in the cornea 1100 of the eye allows one to gain access to the tissue bounding the pocket 1106 (i.e., the interior stromal tissue bounding the pocket 1106). In particular, as shown in the illustrative embodiment of FIG. 43*a*, the pocket 1106 is formed by making an intrastromal incision in the cornea 1100 of the eye using femtosecond laser 1108 (i.e., the incision is cut in the cornea 1100 using the laser beam(s) emitted from the femtosecond laser). In the illustrated embodiment, the pocket 1106 is cut in the cornea 1100 of the eye so as to have a diameter between about 10 millimeters and about 13 millimeters, inclusive (or a diameter between 10 millimeters and 13 millimeters, inclusive). As such, the diameter of the pocket 1106 is substantially equal to, or equal to the overall diameter of the cornea 1100 from one side of the limbus to the other side of the limbus. In an alternative embodiment, the intrastromal incision in the cornea 1100 may be formed using a mechanical keratome or a mechanical microkeratome. Advantageously, the forming of the pocket 1106 with the femtosecond laser or the mechanical keratome reduces the postoperative pain sensation that is felt by a patient when the front surface of the cornea is ablated, as will be described hereinafter with regard to FIG. 43*d*.

Figure 43B:
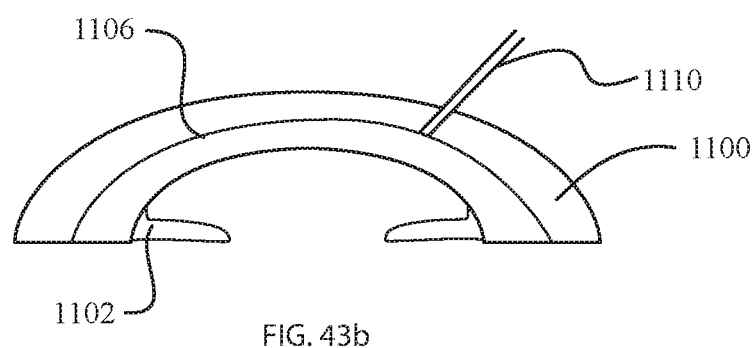
FIG. 43b is yet another partial side cross-sectional view of the eye of FIG. 43a illustrating the application of a photosensitizer inside the pocket.

Turning to FIG. 43*b*, it can be seen that, after the pocket 1106 is cut using the femtosecond laser 1108, a photosensitizer is applied inside the pocket so that the photosensitizer permeates the tissue bounding the pocket 1106. The photosensitizer facilitates the cross-linking of the tissue bounding the pocket 1106. In the illustrated embodiment of FIG. 43*b*, the photosensitizer is injected with a needle 1110 inside the stromal pocket without lifting the anterior corneal stroma so as to cover the internal surface of the corneal pocket 1106. In one or more embodiments, the photosensitizer or cross-linker that is injected through the needle 1110 inside the stromal pocket comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 1106 may be aspirated through the needle 1110 until all, or substantially all, of the excess portion of the photosensitizer is removed from the pocket 1106 (i.e., the excess cross-linker may be aspirated through the same needle 1110 so that the pocket 1106 may be completely emptied or substantially emptied).

Figure 43C:
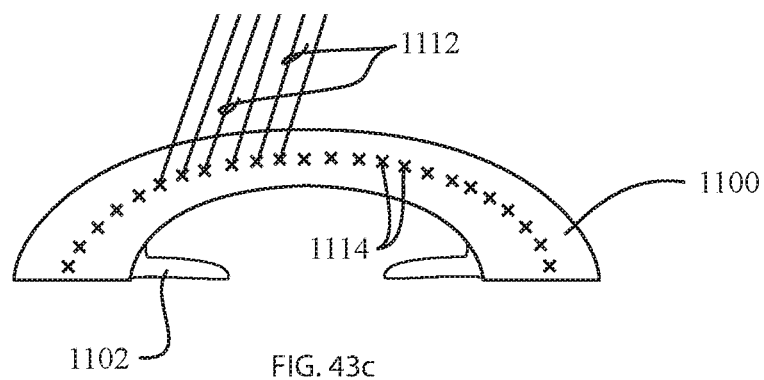
FIG. 43c is still another partial side cross-sectional view of the eye of FIG. 43a illustrating the irradiation of the cornea so as to activate cross-linkers in the portion of the cornea bounding the pocket.

Next, turning to the illustrative embodiment of FIG. 43*c*, shortly after the photosensitizer is applied inside the pocket, the cornea 1100 of the eye is irradiated from the outside using ultraviolet (UV) radiation 1112 so as to activate cross-linkers in the portion of the tissue bounding the pocket 1106 and thereby stiffen the cornea 1100 and prevent corneal ectasia of the cornea 1100 by cross-linking the middle, stromal portion of the cornea 1100 so as to make the cornea 1100 stable (i.e., by stiffening the bounding wall of the pocket 1106). In the illustrative embodiment, the ultraviolet light used to irradiate the cornea 1100 may have a wavelength between about 370 nanometers and about 380 nanometers (or between 370 nanometers and 380 nanometers). Also, in the illustrative embodiment, only a predetermined anterior stromal portion 1114 of the cornea 1100 to which the photosensitizer was applied is cross-linked (i.e., the bounding wall of the corneal pocket 1106), thereby leaving an anterior portion of the cornea 1100 and a posterior stromal portion of the cornea 1100 uncross-linked. That is, in the illustrative embodiment, the entire corneal area 1114 inside the cornea 1100 exposed to the cross-linker is selectively cross-linked, thereby leaving the anterior part of the cornea 1100 and the posterior part of the stroma uncross-linked. The portion of the cornea 1100 without the cross-linker is not cross-linked when exposed to the UV radiation. In an alternative embodiment, the cornea 1100 may be irradiated using microwaves as an alternative to, or in addition to being irradiated using ultraviolet (UV) radiation.

Figure 43D:
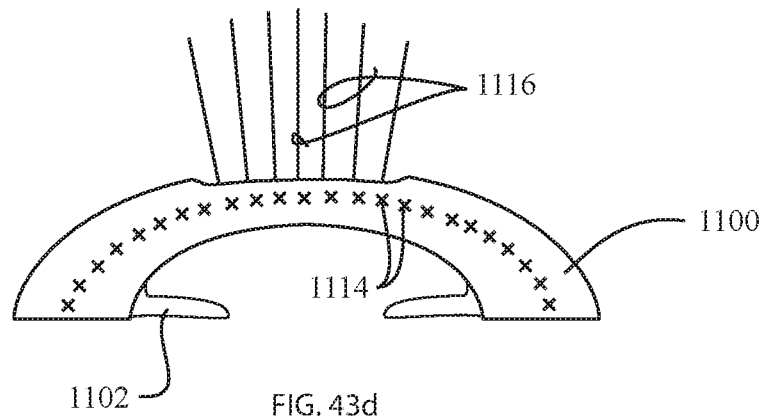
FIG. 43d is yet another partial side cross-sectional view of the eye of FIG. 43a illustrating the ablation of a front surface of the cornea so as to change the refractive properties of the eye.

Now, with reference to FIG. 43*d*, it can be seen that, after the cornea 1100 has been stiffened by the activation of the cross-linkers, a front surface of the cornea 1100 is ablated using an excimer laser 1116 so as to change the refractive properties of the eye (i.e., the anterior cornea 1100 is ablated using the laser beam(s) emitted from the excimer laser). As such, because FIG. 43*d* depicts ablating a front surface of the cornea 1100, the ablation procedure depicted in FIG. 43*d* is in the form of a photorefractive keratectomy (PRK) procedure. The posterior stroma of the eye is uncross-linked. Both of the aforedescribed procedures described with reference to FIGS. 42a-42f and FIGS. 43a-43d eliminate the possibility of post-LASIK corneal ectasia (i.e., corneal ectasia following laser in situ keratomileusis).

In the procedure described above with regard to FIGS. 43a-43d, the anterior part of the cornea 1100 is not cross-linked. The advantage of not cross-linking the anterior part of the cornea 1100 is that it does not require removal of the corneal epithelium for the cross-linker to penetrate inside the stroma (a time consuming process). In addition, if the epithelium is removed to enhance cross-linker penetration, the epithelium does not regrow well over the cross-linked cornea, and the epithelium remains unstable even when it regrows, and thus, it can easily separate from its bed.

Also, an advantage of the procedure illustrated in FIGS. 43a-43d over a conventional photorefractive keratectomy (PRK) procedure is that making a corneal pocket with a femtosecond laser cuts some, but not all the nerves supplying the corneal surface. Thus, the procedure depicted in FIGS. 43a-43d reduces the sever post-PRK pain sensation, which is a serious problem, with the conventional PRK procedure (see e.g., Sobas E. M. et al., "Ocular pain and discomfort after advanced surface ablation: an ignored complaint", Clinical Ophthalmology 2015:9, pp. 1625-1632). The procedure illustrated in FIGS. 43a-43d is particularly beneficial for a myoptic eye.

In addition, the advantage of the procedure illustrated in FIGS. 43a-43d over a standard LASIK procedure with a flap is that by not creating or lifting the corneal flap, not all corneal nerves supplying the corneal surface are cut (i.e., only deep nerves are cut, while the majority of the anterior corneal nerve plexus remains intact so as to avoid the lack of sensation that results in dry eye). Therefore, this technique prevents dry eye formation which is a complication of the standard LASIK procedure. Regrowth of the nerves after the standard LASIK procedure takes approximately 3-12 months. The standard LASIK procedure should therefore be avoided in diabetic patients because of their poor wound healing tendency and their higher likelihood of developing a postoperative dry eye.

Advantageously, in the procedure illustrated in FIGS. 43a-43d, the incision made by the femtosecond laser 1108 to form the corneal pocket 1106 does not significantly damage the anterior sub-epithelial nerve plexus. In stark contrast, the sub-epithelial corneal nerve plexus can be seriously compromised by an extended external incision as is done for a LASIK flap creation or an anterior cross-linking procedure that involves the anterior corneal nerve plexus. In addition, the corneal epithelium is not stable and does not heal well over an anterior cross-linked corneal surface. Slightly more than one-half of the sub-epithelial corneal plexus is supplied by the superficial branches of the corneal nerves which contribute to sub-epithelial corneal plexus that enter the cornea from the limbus from all sides. Creating the femtosecond laser pocket 1106 in FIG. 43b, cuts less than one-half of the nerve supply to the anterior corneal sub-epithelial plexus and thus, does not cause significant or lasting dry eye in a normal eye because the majority of the superficial sub-epithelial corneal nerve plexus remains intact.

Figure 44:
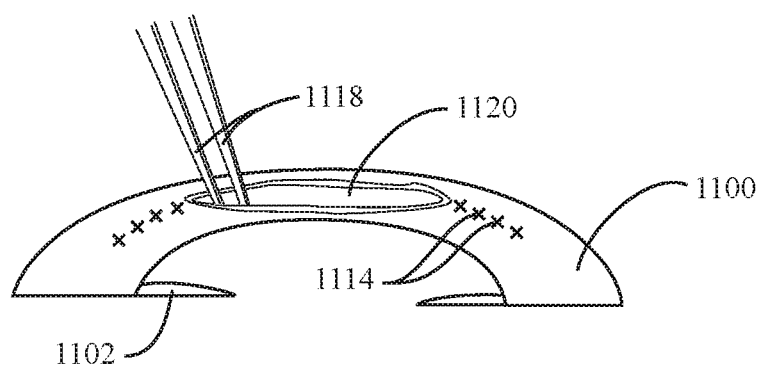
FIG. 44 is still another partial side cross-sectional view of the eye of FIG. 43a illustrating the insertion of a lens implant into the pocket so as to change the refractive properties of the eye, according to an alternative embodiment of the invention.

Referring now to FIG. 44, an alternative manner in which the refractive properties of the eye may be modified in the procedure described above is shown. For this alternative embodiment, the steps illustrated in FIGS. 43a-43c are performed in the same manner as that described above. However, rather than ablating the front surface of the cornea 1100 as explained above with regard to FIG. 43d, a lens implant or lenticle 1120 is inserted into the corneal pocket 1106 in order to change the refractive properties of the eye (refer to FIG. 44). In particular, in the illustrated embodiment, the lens implant or lenticle 1120 is inserted into the corneal pocket 1106 using forceps or microforceps 1118. In one or more embodiments, the lens implant or lenticle 1120 may comprise a suitable transparent polymeric organic or synthetic lens. The surface of the lens implant 1120 may have the appropriate shape to reshape the cornea 1100 or the dioptric power to nullify the remaining spheric or astigmatic error of the eye. The implantation of an inlay or lenticle 1120, or the use of an excimer laser for surface ablation, may be done at any time after the internal stromal structure is cross-linked by using the UV radiation 1112.

Turning again to FIG. 43a, in this lens implant embodiment, the corneal pocket 1106 formed in the cornea 1100 of the eye may be in the form of an intrastromal corneal pocket cut into the corneal stroma.

In one embodiment, the diameter of the corneal pocket 1106 may be from 1 millimeter (mm) to 12 millimeters (mm) as needed.

Figure 46A:
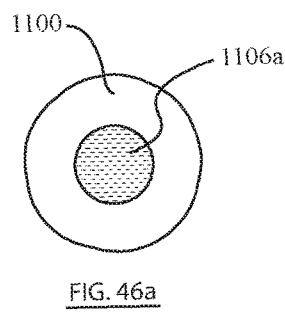
FIG. 46a is a frontal view of a cornea of an eye illustrating a central corneal pocket formed in the cornea of the eye, according to an embodiment of the invention.
Figure 46B:
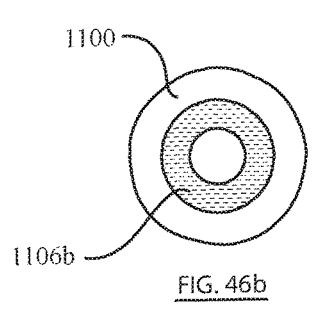
FIG. 46b is a frontal view of a cornea of an eye illustrating a central doughnut or ring-shaped pocket formed in the cornea of the eye around the visual axis, according to another embodiment of the invention.
Figure 46C:
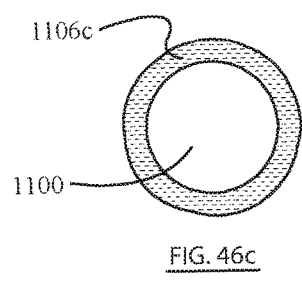
FIG. 46c is a frontal view of a cornea of an eye illustrating a peripheral doughnut or ring-shaped pocket formed in the cornea of the eye, according to yet another embodiment of the invention.

As shown in FIG. 46a, the corneal pocket may be in the form of a disk-shaped pocket 1106a centrally disposed over the visual axis. Alternatively, as depicted in FIG. 46b, the corneal pocket may be in the form of a central doughnut-shaped or ring-shaped pocket 1106b disposed around the central visual axis. Further, in another embodiment, the corneal pocket may be in the form of a peripheral doughnut-shaped or ring-shaped pocket 1106c (refer to FIG. 46c).

Now, with reference again to FIG. 43b, it can be seen that, after the pocket 1106 is cut using the femtosecond laser 1108, a photosensitizer is applied inside the pocket so that the photosensitizer permeates the tissue bounding the pocket 1106. In one embodiment, a photosensitizer, such as riboflavin, is injected (e.g., using needle 1110) in a desired concentration of from about 0.2% to about 4% (0.2% to 4%) in a biocompatible fluid and a volume of 0.02-1 milliliters (ml) inside the corneal pocket 1106.

In one embodiment, the photosensitizer, such as riboflavin, is injected at the desired concentration of from about 0.2% to about 4% (0.2% to 4%) in a biocompatible fluid in the corneal pocket 1106 so as to sufficiently to cover the internal wall of the pocket 1106 for a desired duration so that it penetrates at least 20 microns and beyond in the corneal pocket 1106 inside the corneal stroma prior to a corneal implantation of an inlay, thereby preventing rejection of an implant by cellular proliferation or encapsulation of the implant.

Next, referring again to FIG. 43c, after the photosensitizer is applied inside the pocket, the cornea 1100 of the eye is irradiated using ultraviolet (UV) radiation 1112 so as to activate cross-linkers in the portion of the tissue bounding the pocket 1106 and thereby stiffen the cornea 1100. In one embodiment, the wall of the pocket 1106 is radiated either from outside the cornea 1100 or inside the cornea 1100 with a ultraviolet (UV) or other appropriate radiation to cross-link the wall of the pocket 1106, thereby crosslinking the corneal collagen stained with the crosslinker and killing the cells contained therein, while the remaining cornea 1100 is not crosslinked. In one or more embodiments, the intensity of the ultraviolet (UV) radiation varies from 1 mW/mm$^2$ to 30 mW/mm$^2$ for a time duration of 0.5-15 minutes to complete the crosslinking, and to create a space that will not adhere to itself or to an implant, or produce an antibody in response to a foreign implant (because there are no cells to respond to the foreign implant in the cross-linked area).

In one embodiment, the ultraviolet UV radiation at the desired power from about 1 mW/mm$^2$ to about 30 mW/mm$^2$ (or from 1 to 30 mW/mm$^2$), or more preferably, from about 1 mW/mm$^2$ to about 10 mW/mm$^2$ (or from 1 to 10 mW/mm$^2$) is applied to the wall of the pocket 1106 for a duration of 1-15 minutes, or preferably less, as needed depending on the concentration of the photosensitizer (e.g. riboflavin or another photosensitizer). The wall of the pocket 1106 also may be radiated with another visible or infrared (IR) wavelength of light applied externally to activate the photosensitizer in the corneal pocket 1106, and to crosslink the collagen of the corneal stroma surrounding the corneal pocket 1106, thereby killing all cells located within the areas of the cornea 1100 that contains the cross-linker so as to prevent rejection or encapsulation of the implant 1120, while providing physical stability to the cornea 1100 and preventing the walls of the pocket 1106 from adhering together or from adhering to the implant 1120.

In one embodiment, the crosslinking described above is done repeatedly after the inlay 1120 is implanted so as to prevent any cellular invasion in the area surrounding the implant 1120.

Finally, with reference once again to FIG. 44, a lens implant or inlay 1120 is inserted into the corneal pocket 1106 in order to change the refractive properties of the eye. In one embodiment, the pocket 1106 is filled with a biocompatible inlay 1120 of cross-linked organic material, non-organic material, a mixture of organic and non-organic material, or corneal tissue. The inlay 1120 has a desired thickness of 20 microns to 400 microns and a flat shape, convex shape, concave shape, or a combination of these different shapes.

In another embodiment, the lens implant or inlay 1120 may be in the form of a polymeric implant with a water content of from 1% to 96%.

Figure 47A:
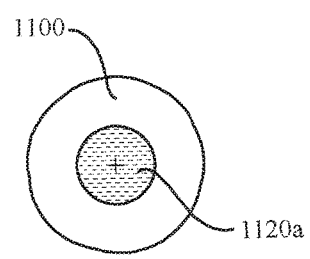
FIG. 47a is a frontal view of a cornea of an eye illustrating a central location of a lens implant in the cornea of the eye, according to an embodiment of the invention.
Figure 47B:
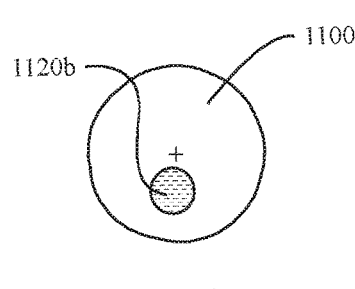
FIG. 47b is a frontal view of a cornea of an eye illustrating an off-center location of a lens implant in the cornea of the eye, according to another embodiment of the invention.
Figure 47C:
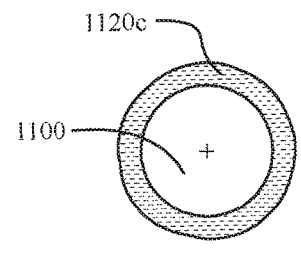
FIG. 47c is a frontal view of a cornea of an eye illustrating a peripheral location of a lens implant in the cornea of the eye, according to yet another embodiment of the invention.
Figure 47D:
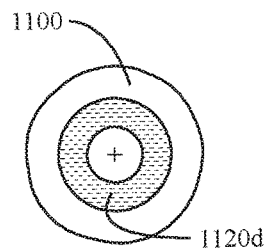
FIG. 47d is a frontal view of a cornea of an eye illustrating a central location of a lens implant in the cornea of the eye around the visual axis, according to still another embodiment of the invention.
Figure 47E:
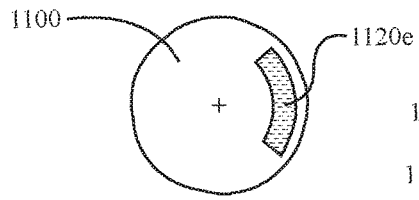
FIG. 47e is a frontal view of a cornea of an eye illustrating a location of a first partial lens implant in the cornea of the eye, according to yet another embodiment of the invention.
Figure 47F:
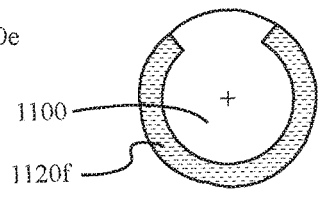
FIG. 47f is a frontal view of a cornea of an eye illustrating a location of a second partial lens implant in the cornea of the eye, according to still another embodiment of the invention.

In still another embodiment, the lens implant or inlay 1120 may be located at a predetermined distance from the Bowman's membrane or from the corneal periphery, and may be located in the center of the visual axis (see FIG. 47a), or off-center relative to the visual axis (e.g., refer to the implant 1120b in FIG. 47b).

In yet another embodiment after the implantation of the initial lens implant or inlay 1120, the remaining refractive error of the eye may be corrected with a subsequent implant or inlay. That is, the initial implant or inlay 1120 may be removed and replaced with another implant or inlay to correct the remaining refractive error of the eye. That is, the implant or inlay 1120 may be easily replaced as the eye grows and requires a new refraction.

In still another embodiment, the corneal pocket 1106 is used to change the refractive power of the cornea 1100 by receiving a lens structure that is capable of modifying the refractive power of the eye either by its refractive index or by its surface curvature of the lens, which affects the corneal curvature overlaying the implant or inlay 1120. The inlay 1120 may be formed from any transparent organic biocompatible material, non-organic biocompatible material, synthetic biocompatible material, or a combination of these biocompatible materials.

In yet another embodiment, the size of the implant or inlay 1120 may be 1 to 12 millimeters (mm) in diameter, and may have a thickness of between 10 to 200 microns with one micron or larger sized holes so as to allow the diffusion of fluid across the inlay 1120.

In yet another embodiment, the holes made in the implant or inlay 1120 may be of any size in the peripheral inlay (e.g., 1 to 100 microns or more) if the inlay 1120 is larger than five millimeters (mm) in diameter, while the holes inside the central 5 millimeters (mm) of the inlay 1120 may be about 0.1 microns to about 4 microns in diameter.

In still another embodiment, the implant or inlay 1120 may have a dioptric power of plus or minus 1 to 20 diopters.

In yet another embodiment, the implant or inlay 1120 corrects the spherical error, astigmatic error, or a combination of the spherical and astigmatic of the eye.

In still another embodiment, the size of the implant or inlay 1120 may be between 2 to 4 millimeters (mm) in diameter, and may be located slightly off-center from the visual axis inferiorly for correction of presbyopia eyes with a dioptric power of +1 to 4 diopters. Alternatively, the implant or inlay 1120 may be centered over the visual axis for correction of myopia, hyperopia, or astigmatism (e.g., refer to the implant 1120a in FIG. 47a).

In still another embodiment, the implant or inlay 1120 may be a central doughnut-shaped implant (e.g., refer to the implant 1120d in FIG. 47d), which is centered around the visual axis for creation of a bifocal cornea (e.g., for both far and/or near vision). Alternatively, the inlay 1120 may be in the form of a peripheral ring or may be doughnut-shaped so as to surround the visual axis in order to treat degenerative peripheral corneal diseases (e.g., refer to the implant 1120c in FIG. 47c). Also, rather than comprising a complete ring, the implant or inlay 1120 may be in the form of a partial sectorial implant 1120e, such as that illustrated in FIG. 47e. Similarly, the implant or inlay 1120 may be in the form of a larger partial implant 1120f, such as that shown in FIG. 47f (i.e., an implant 1120f that extends around a greater portion of the circumference of the cornea 1100).

In yet another embodiment, the degree of the correction may be expanded from the presently allowed plus or minus 7.00 diopters, which is approved by the FDA for the LASIK procedure, to a much greater plus or minus 20 dioptric power for spherical correction, or plus or minus 6 dioptric power for astigmatism using the inlay 1120 to correct the refractive error of the eye.

In still another embodiment, the implant or inlay 1120 is used to provide structural stability to the cornea 1100 for treating eye conditions, such as keratoconus. When treating such conditions, the inlay 1120 can be a large thin circulate plate made of a cross-linked collagen with a mesh of graphene having holes in it, or other nanoparticles that are implanted in the cross-linked corneal pocket 1106 so as to add to the stability of the cornea 1100 and prevent the rejection or encapsulation of the inlay 1120.

In yet another embodiment, the repeated crosslinking of the pocket 1106 may be performed as needed to prevent new cellular ingrowth and adhesion around the implant 1120 so that the implant 1120 is capable of being removed and replaced with ease, as needed (e.g., as the eyes grow in children etc.).

In another embodiment, after the cornea 1100 has been stiffened by the activation of the cross-linkers, the front surface of the cornea 1100 is ablated so as to further alter the refractive properties of the eye and to eliminate any residual refractive error remaining after initial refractive error correction by the lens implant 1120 of FIG. 44. That is, in this alternative embodiment, the steps illustrated in FIGS. 43a-43c are performed in the same manner as that described above, then the lens implant 1120 is inserted into the corneal pocket 1106 to change the refractive properties of the eye (as described above in conjunction with FIG. 44), and finally any residual refractive errors remaining after the initial refractive error correction by the lens implant 1120 are corrected by the front surface ablation of the cornea 1100, which is in the form of a photorefractive keratectomy (PRK)

procedure. Also, in this embodiment, the lens implant 1120 may be inserted into the corneal pocket 1106 prior to the cross-linking of the cornea 1100, or after the cross-linking of the cornea 1100.

In still another embodiment, after the corneal inlay placement, further correction of the refractive error of the eye may be done with a mini-PRK procedure of 0.2-2 dioptric power and a smaller diameter of the PRK, which is limited to 3-5 millimeters (mm) of the central cornea.

In yet another embodiment, the implant or inlay 1120 with a cross-linker disposed thereon is inserted into the corneal pocket 1106 through a small external incision made into the corneal pocket 1106 with a micro-knife or a femtosecond laser, and is then subsequently cross-linked. The remaining refractive error of the eye is corrected by performing a PRK procedure after the lens implantation utilizing an excimer laser. The diameter or the size of the PRK area depends on various factors but, in general, may vary between 4-6 millimeters (mm) or 6-9 millimeters (mm) or more around the visual axis. This procedure reduces the pain sensation after PRK that, in general, is associated with a sever pain sensation. In addition, it eliminates the dry eye complication that occurs after the LASIK procedure.

In still another embodiment, the inlay corrects a part of the refractive power of the eye, while PRK corrects the remaining refractive power of the cornea 1100 for spherical, astigmatism or combination thereof under simultaneous control of a Shack-Hartmann system.

In yet another alternative embodiment, the method of altering the refractive properties of the eye may further comprise forming an additional pocket in the cornea 1100 of the eye of the patient so as to gain access to tissue bounding the additional pocket. That is, in this alternative embodiment, the method comprises the additional steps of: (i) forming an additional pocket in the cornea 1100 of the eye of the patient so as to gain access to tissue bounding the additional pocket, wherein the forming of the additional pocket in the cornea of the eye severs some corneal nerves supplying the front surface of the cornea 1100 so as to reduce the postoperative pain sensation that is felt by the patient, but does not sever all of the corneal nerves supplying the front surface of the cornea 1100 so as to prevent a formation of dry eye in the patient; (ii) after the additional pocket in the cornea 1100 has been formed, applying the photosensitizer inside the additional pocket so that the photosensitizer permeates at least a portion of the tissue bounding the additional pocket, the photosensitizer facilitating cross-linking of the tissue bounding the additional pocket; and (iii) further irradiating the cornea 1100 so as to activate cross-linkers in the portion of the tissue bounding the additional pocket and thereby stiffen the cornea 1100 and prevent corneal ectasia of the cornea 1100.

In still another alternative embodiment, after the intrastromal pocket 1106 is formed and cross linking is performed, the remaining refractive error of the eye may be corrected by implanting or injecting a flexible organic or a porous synthetic polymer or a mixture of surface modified transparent polymers, such as hydrogel etc., having a very high water content of up to 90%, in the corneal pocket 1106. The porous polymers may be created by known methods utilizing anodization, stain etching, or bottom up synthesis. And then subsequently, the polymers may be subjected to slow evaporation to dry them. Subsequent surface modification stabilizes the polymer and improves biocompatibility. In an exemplary embodiment, the flexible organic or porous synthetic polymer or mixture of surface modified transparent polymers may be injected through a 2-3 millimeter (mm) opening in the cornea 1100 using an instrument, such as an intraocular lens injector, along with a viscous fluid. The center of the implant is placed over the visual axis of the eye using a bent dull needle or the axis of the astigmatism is aligned and corrected with a toric inlay. This inlay has a side marking indicating the location of astigmatic axis. The intrastromal crosslinking prevents overgrowth of the fibroblast on the implant and the implant corrects the refractive error by its defined surface curvature.

In the procedure described above with regard to FIGS. 43*a*-43*d*, the intrastromal cross-linking was performed prior to the ablation of the corneal surface. That is, the corneal surface ablation is performed at a later time when the cornea 1100 is stable, and when the refractive errors can be accurately analyzed and corrected. In an exemplary embodiment, the time period before corneal surface ablation may be 2-3 weeks after the crosslinking to benefit from reduced corneal sensation after the formation of the intrastromal pocket. However, in an alternative embodiment, the corneal surface ablation may be done first, and then thereafter, the corneal stromal incision is created with the femtosecond laser, followed by the crosslinking inside the corneal stroma. In this alternative embodiment, the corneal intrastromal incision and the intrastromal crosslinking may be performed immediately after the corneal surface ablation, or a predetermined time period after the corneal surface ablation. Preferably, in this alternative embodiment, the intrastromal crosslinking is performed immediately after the corneal surface ablation to get the benefit of reduced corneal sensation by reducing the pain sensation felt by the patient.

Yet another illustrative embodiment of a method of altering the refractive properties of an eye is shown in FIGS. 45*a*-45*d*. In general, the procedure illustrated in these figures involves soaking a lens implant in a crosslinking solution, forming a pocket in the cornea of an eye, inserting the lens implant in the pocket, and then cross-linking the interior stroma. In this embodiment, no flap is formed in the cornea 1206 of the eye. Referring initially to the diagrammatic view of FIG. 45*b*, it can be seen that the eye undergoing ablation generally includes a cornea 1206 and an iris 1208.

Figure 45A:
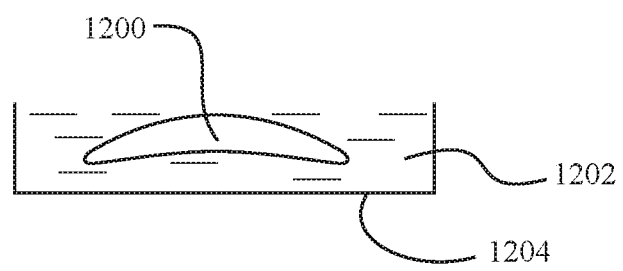
FIG. 45a is a partial side cross-sectional view of a lens implant being soaked in a cross-linking solution that includes a photosensitizer, according to yet another embodiment of the invention.

First of all, as shown in FIG. 45*a*, a lens implant 1200 is soaked in a cross-linking solution 1202 held in a container 1204 prior to its insertion into a corneal pocket in the eye so that the lens implant 1200 is pre-coated with the cross-linking solution 1202 thereon. The lens implant 1200 has a predetermined shape for changing the refractive properties of an eye. In the illustrative embodiment, the lens implant 1200 may be made from any organic or synthetic polymeric material, another cornea, tissue culture grown stromal material, etc. Also, in the illustrative embodiment, the cross-linking solution 1202 comprises a photosensitizer in the form of riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein).

Figure 45B:
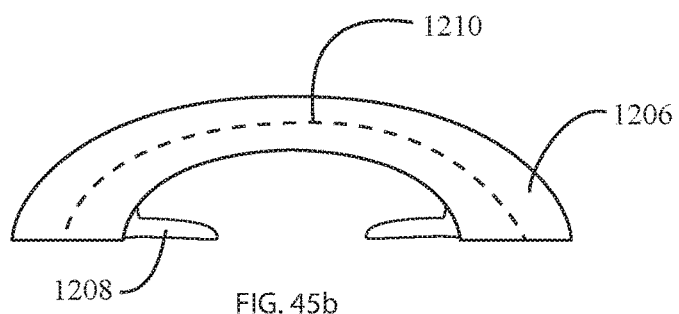
FIG. 45b is a partial side cross-sectional view of an eye on which a procedure for altering the refractive properties of the eye using the lens implant of FIG. 45a is performed, wherein the forming of a pocket using an intrastromal incision is illustrated in this figure.

In FIG. 45*b*, the forming of a large corneal pocket 1210 in the cornea 1206 of the eye is diagrammatically illustrated. The formation of the large corneal pocket 1210 in the cornea 1206 of the eye allows one to gain access to the tissue bounding the pocket 1210 (i.e., the interior stromal tissue bounding the pocket 1210). In particular, in the illustrative embodiment, the pocket 1210 is formed by making an intrastromal incision in the cornea 1206 of the eye using a femtosecond laser (i.e., the incision is cut in the cornea 1206 using the laser beam(s) emitted from the femtosecond laser). In an alternative embodiment, the intrastromal incision in the cornea 1206 may be formed using a mechanical keratome or a mechanical microkeratome.

Figure 45C:
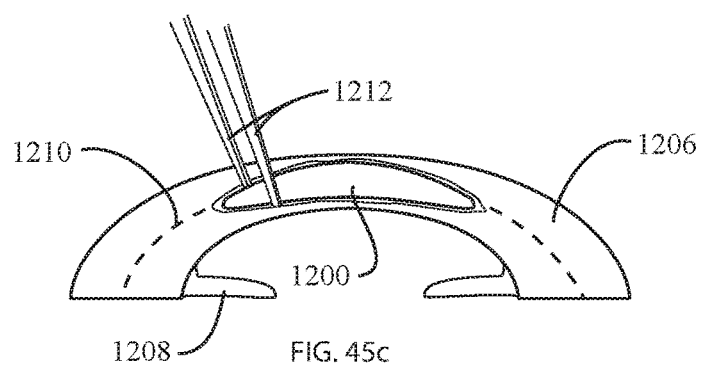
FIG. 45c is another partial side cross-sectional view of the eye of FIG. 45b illustrating the insertion of the lens implant of FIG. 45a into the pocket so as to change the refractive properties of the eye.

Turning to FIG. 45c, it can be seen that, after the pocket 1210 is cut using the femtosecond laser, the lens implant 1200 with the photosensitizer provided thereon (e.g., riboflavin) is inserted inside the pocket 1210 so that the photosensitizer permeates at least a portion of the tissue bounding the pocket 1210. In particular, in the illustrated embodiment, the lens implant 1200 is inserted into the corneal pocket 1210 through a small side incision using a pair of forceps or microforceps 1212. The photosensitizer facilitates the cross-linking of the portion of the tissue bounding the pocket 1210.

In this embodiment, the implant 1200, which was initially dipped in a photosensitizer, is implanted in the corneal pocket 1210 so as to allow the photosensitizer to diffuse out of the implant 1200 into the tissue surrounding the implant prior to the application of the ultraviolet (UV) radiation with a desired power and duration being applied so as to crosslink the collagen of the corneal stroma surrounding the corneal pocket 1210, thereby killing all cells located within the cross-linked cornea and the cross-linked inlay simultaneously, while providing a physical stability to the cornea without gluing the wall of the pocket 1210 together, or to the implant 1200. Also, rather using ultraviolet (UV) radiation, other types of radiation with a suitable wavelength or microwaves may be applied externally to perform the cross-linking.

Figure 45D:
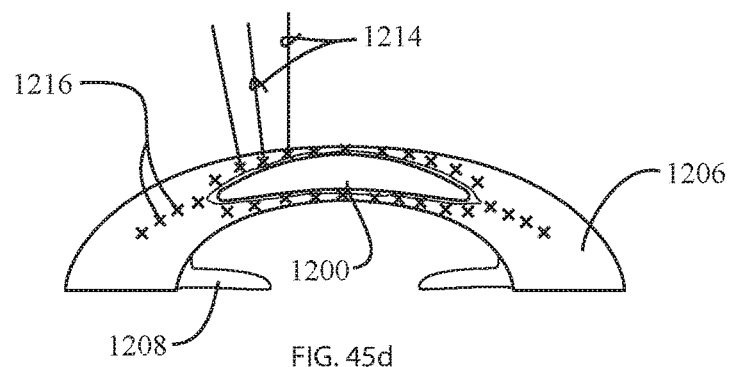
FIG. 45d is yet another partial side cross-sectional view of the eye of FIG. 45b illustrating the irradiation of the cornea so as to activate cross-linkers in the portion of the cornea bounding the pocket.

Next, referring to the illustrative embodiment of FIG. 45d, shortly after the lens implant 1200 with the photosensitizer is inserted inside the pocket 1210, the cornea 1206 of the eye is irradiated from the outside using ultraviolet (UV) radiation 1214 so as to activate cross-linkers in the portion of the tissue bounding the pocket 1210 and thereby stiffen the cornea 1206 and prevent corneal ectasia of the cornea 1206. In the illustrative embodiment, the ultraviolet light used to irradiate the cornea 1206 may have a wavelength between about 370 nanometers and about 380 nanometers (or between 370 nanometers and 380 nanometers). Also, in the illustrative embodiment, only a predetermined anterior stromal portion 1216 of the cornea 1206 to which the photosensitizer was applied is cross-linked (e.g., only the bounding wall of the corneal pocket 1210—see FIG. 45d), thereby leaving an anterior portion of the cornea 1206 and a posterior stromal portion of the cornea 1206 uncross-linked. That is, in the illustrative embodiment, the entire corneal area 1216 inside the cornea 1206 exposed to the cross-linker is selectively cross-linked, thereby leaving the anterior part of the cornea 1206 and the posterior part of the stroma uncross-linked. The portion of the cornea 1206 without the cross-linker is not cross-linked when exposed to the UV radiation. In an alternative embodiment, the cornea 1206 may be irradiated using microwaves as an alternative to, or in addition to being irradiated using ultraviolet (UV) radiation.

Advantageously, the internal crosslinking strengthens the corneal resistance against the intraocular pressure and prevents corneal ectasia of a thin cornea that occurs when a LASIK procedure is done on such a thin cornea, and in case of implantation of an inlay, the corneal stroma surrounding the pocket is devoid of keratocytes after crosslinking. As such, the cross-linked eye will not mount a rejection response to an intracorneal implant.

Figure 45E:
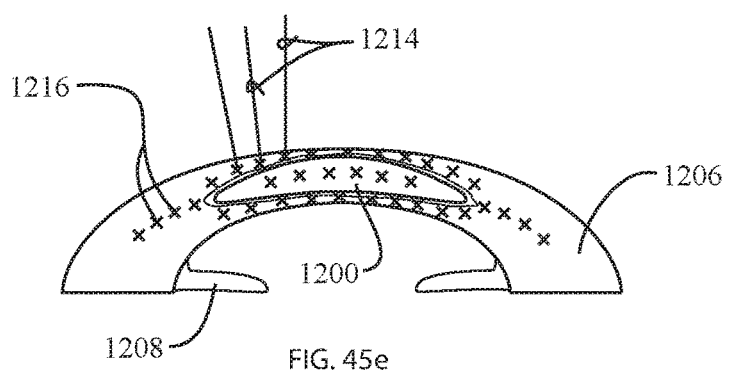
FIG. 45e is still another partial side cross-sectional view of the eye of FIG. 45b illustrating the simultaneous irradiation of both the cornea and a porous lens implant, according to another alternative embodiment of the invention.

Referring now to FIG. 45e, an alternative type of lens implant 1200 may be inserted inside the corneal pocket 1210. For this alternative embodiment, the steps illustrated in FIGS. 45a-45c are performed in the same manner as that described above. However, the lens implant 1200 of FIG. 45e, which is used to change the refractive power of the cornea 1206, is a porous polymeric implant, a porous organic or non-organic implant, or a 3D-printed porous implant. The porous implant may be flexible or semi-flexible, and may be any shape or size that is capable of being implanted through a small side incision (e.g., using forceps or microforceps). When the lens implant 1200 is an organic lens, it may comprise a tissue culture grown lens or simply corneal tissue, such as a transplant. After implantation, the photosensitizer (e.g., riboflavin) diffuses out of the lens implant 1200, and into the corneal stroma. Similar to that described above with regard to FIG. 45d, in the alternative embodiment of FIG. 45e, the cornea 1206 of the eye is irradiated from the outside through the corneal surface using ultraviolet (UV) radiation 1214 so as to activate cross-linkers in the portion of the tissue bounding the pocket 1210 and thereby stiffen the cornea 1206 and prevent corneal ectasia of the cornea 1206. However, because the lens implant 1200 of FIG. 45e is porous, the lens implant 1200 in FIG. 45e is capable of being cross-linked simultaneously with the corneal stroma to stabilize the lens implant 1200 and cross-link the stroma at the same time.

This procedure or any of the procedures described herein can be used alone, or in conjunction with, simultaneously with, before or after any other procedure, method or device that would alter, correct or enhance the refractive properties of the eye. Additionally, any of the herein described embodiments can be used with any combination of the other embodiments.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of altering the refractive properties of an eye, said method comprising the steps of:
    forming a pocket in a cornea of an eye of a patient so as to gain access to tissue bounding the pocket, wherein the forming of the pocket in the cornea of the eye severs some corneal nerves supplying a front surface of the cornea so as to reduce the postoperative pain sensation that is felt by the patient, but does not sever all of the corneal nerves supplying the front surface of the cornea so as to prevent a formation of dry eye in the patient;
    after the pocket in the cornea has been formed, applying a photosensitizer inside the pocket so that the photosensitizer permeates at least a portion of the tissue bounding the pocket, the photosensitizer facilitating cross-linking of the tissue bounding the pocket;
    inserting a lens implant into the pocket so as to change the refractive properties of the eye; and
    irradiating the cornea so as to activate cross-linkers in the portion of the tissue bounding the pocket and thereby stiffen the cornea and prevent corneal ectasia of the cornea;
    wherein the cross-linking of the tissue bounding the pocket does not adhere the lens implant to the tissue bounding the pocket so that the lens implant is capable of being subsequently replaced, and the cross-linking of the tissue bounding the pocket does not adhere spaced apart portions of the tissue bounding the pocket to one another.

2. The method according to claim 1, wherein the step of forming the pocket in the cornea of the eye severs less than one-half of the corneal nerves supplying the anterior corneal sub-epithelial plexus so as to prevent the formation of dry eye in the patient.

3. The method according to claim 1, wherein the step of forming the pocket in the cornea of the eye comprises forming the pocket in stromal tissue of the cornea.

4. The method according to claim 1, wherein the pocket formed in the cornea of the eye has a diameter between about 1 millimeter and about 12 millimeters.

5. The method according to claim 1, wherein the pocket formed in the cornea of the eye has a shape selected from the group consisting of: (i) a disk shape, (ii) a ring or doughnut shape, and (iii) a sectorial shape.

6. The method according to claim 1, wherein the photosensitizer comprises riboflavin in a biocompatible fluid, the riboflavin being provided in a concentration of between approximately 0.2% and approximately 4.0% in the biocompatible fluid; and
wherein the step of applying the photosensitizer inside the pocket comprises injecting the biocompatible fluid containing the riboflavin inside the pocket using a needle.

7. The method according to claim 6, wherein the biocompatible fluid containing the riboflavin is injected into the pocket for a time duration that is sufficient to enable the riboflavin to penetrate at least 20 microns into the tissue bounding the pocket.

8. The method according to claim 1, further comprising the step of:
applying the photosensitizer inside the pocket one or more additional times and irradiating the cornea one or more additional times to cross-link the tissue bounding the pocket so as to prevent any cellular invasion in an area surrounding the lens implant after the initial implantation of the lens implant without adhering the lens implant to the tissue bounding the pocket and without adhering the spaced apart portions of the tissue bounding the pocket to one another.

9. The method according to claim 1, wherein the lens implant has a thickness between approximately 10 microns and approximately 400 microns.

10. The method according to claim 1, wherein the lens implant has a shape selected from the group consisting of: (i) a disk shape, (ii) a ring or doughnut shape, and (iii) a sectorial shape.

11. The method according to claim 1, further comprising the step of:
replacing the lens implant with a new lens implant in order to correct the remaining refractive error of the eye or to correct a new refractive error that has developed in the eye.

12. The method according to claim 1, wherein the lens implant has a predetermined refractive index and a predetermined curvature, and wherein one or both of the predetermined refractive index and the predetermined curvature of the lens implant are used to change the refractive properties of the eye.

13. The method according to claim 1, wherein the lens implant is formed from a transparent organic biocompatible material, a transparent synthetic biocompatible material, or a combination of a transparent organic biocompatible material and a transparent synthetic biocompatible material.

14. The method according to claim 1, wherein the lens implant has a plurality of holes disposed therein, each of the plurality of holes having a hole diameter between approximately 0.1 microns and approximately 100 microns.

15. The method according to claim 14, wherein the lens implant comprises a first subset of the plurality of holes within a central region and a second subset of the plurality of holes within a peripheral region outside the central region, the central region having a diameter of 5 millimeters; and
wherein each of the first subset of the plurality of holes has a hole diameter between approximately 0.1 microns and approximately 4 microns, and each of the second subset of the plurality of holes has a hole diameter between approximately 1 micron and approximately 100 microns.

16. The method according to claim 1, wherein the lens implant has a dioptric power between −20 diopters and +20 diopters for spherical correction and a dioptric power between −6 diopters and +6 diopters for correction of astigmatism.

17. The method according to claim 1, wherein the lens implant is disposed in a corneal location selected from the group consisting of: (i) a center location over the visual axis of the eye for correcting myopia, hyperopia, or astigmatism, (ii) an off-center location from the visual axis of the eye for correcting presbyopia, (iii) a location surrounding a central portion of the cornea, but not overlapping the visual axis of the eye for creating a bifocal cornea, (iv) a location circumscribing a peripheral portion of the cornea for treating a peripheral degenerative corneal disease, and (v) a peripheral location overlapping a sectorial portion of the cornea.

18. The method according to claim 1, wherein the lens implant comprises a circular plate made of a cross-linked collagen so as to add structural rigidity to the cornea of the eye; and wherein the method further comprises the step of:
implanting a mesh formed from nanoparticles into the pocket formed in the cornea so as to add further structural rigidity to the cornea of the eye.

19. The method according to claim 18, wherein the nanoparticles forming the mesh comprise graphene.

20. The method according to claim 1, further comprising the step of:
after the lens implant has been inserted into the pocket, ablating the front surface of the cornea so as to further alter the refractive properties of the eye and to eliminate any residual refractive error remaining after initial refractive error correction by the lens implant.

21. The method according to claim 20, wherein the step of ablating a front surface of the cornea so as to change the refractive properties of the eye comprises performing a mini-photorefractive keratectomy (mini-PRK) procedure on the front surface of the cornea, the mini-PRK procedure being limited to a central region of the cornea having a diameter between approximately 3 millimeters and 5 millimeters, and the mini-PRK procedure resulting in a dioptric power correction of between 0.2 diopters and 2 diopters.

* * * * *